US009376492B2

(12) United States Patent
Chen

(10) Patent No.: US 9,376,492 B2
(45) Date of Patent: Jun. 28, 2016

(54) TREATMENT OF CANCER

(75) Inventor: Min-Che Chen, Manchester (GB)

(73) Assignee: Asclepiumm Limited, Manchester (GB)

( * ) Notice: Subject to any disclaimer, the term of this patent is extended or adjusted under 35 U.S.C. 154(b) by 111 days.

(21) Appl. No.: 13/497,562

(22) PCT Filed: Sep. 22, 2010

(86) PCT No.: PCT/GB2010/001776
§ 371 (c)(1), (2), (4) Date: Jul. 5, 2012

(87) PCT Pub. No.: WO2011/036440
PCT Pub. Date: Mar. 31, 2011

(65) Prior Publication Data
US 2012/0276082 A1 Nov. 1, 2012

(30) Foreign Application Priority Data
Sep. 23, 2009 (GB) .................................. 0916686.9

(51) Int. Cl.
*A61K 39/395* (2006.01)
*C07K 16/28* (2006.01)
*C07K 14/705* (2006.01)
*A61P 35/04* (2006.01)
*G01N 33/50* (2006.01)
*A61K 38/00* (2006.01)

(52) U.S. Cl.
CPC ........... *C07K 16/28* (2013.01); *A61K 39/39533* (2013.01); *C07K 14/705* (2013.01); *G01N 33/5011* (2013.01); *A61K 38/00* (2013.01); *C07K 2317/76* (2013.01)

(58) Field of Classification Search
None
See application file for complete search history.

(56) References Cited

U.S. PATENT DOCUMENTS 5,597,725 A * 1/1997 Suzuki .......................... 435/328
6,638,911 B1 * 10/2003 Blaschuk et al. ............ 514/19.1
2005/0203025 A1 9/2005 Blaschuk et al.

FOREIGN PATENT DOCUMENTS

WO 9957149 11/1999
WO 2007047796 4/2007
WO WO 2007/038264 A2 * 4/2007

OTHER PUBLICATIONS

Codony-Servat J et al, "Differential cellular and molecular effects of bortezomib, a proteasome inhibitor, in human breast cancer cells", Molecular Cancer Therapeutics, American Association of Cancer Research US, 2006, vol. 5, No. 3, pp. 665-675.

(Continued)

*Primary Examiner* — Xiaozhen Xie
(74) *Attorney, Agent, or Firm* — Michael Best & Friedrich LLP

(57) ABSTRACT

The present invention relates to agents for use in treating cancer. The agent to be used is an antagonist of Dsg2, wherein the antagonist modulates the function of the amino acid sequence: TQDVFVGSVEELSAAHTLVMKINAT-DADEPNTLNSKISYR (SEQ ID NO:1), or a fragment or variant thereof, of the EC2 domain of Dsg2. Also included in the invention are specific polypeptides and pharmaceutical preparations. Also included in the invention is a method of screening for antagonists of Dsg2, wherein the antagonist modulates the function of the amino acid sequence: TQD-VFVGSVEELSAAHTLVMKINATDADEPNTLNSKISYR (SEQ ID NO: 1), or a fragment or variant thereof, of the EC2 domain of Dsg2.

5 Claims, 8 Drawing Sheets

(56) References Cited

OTHER PUBLICATIONS

Figure 1:
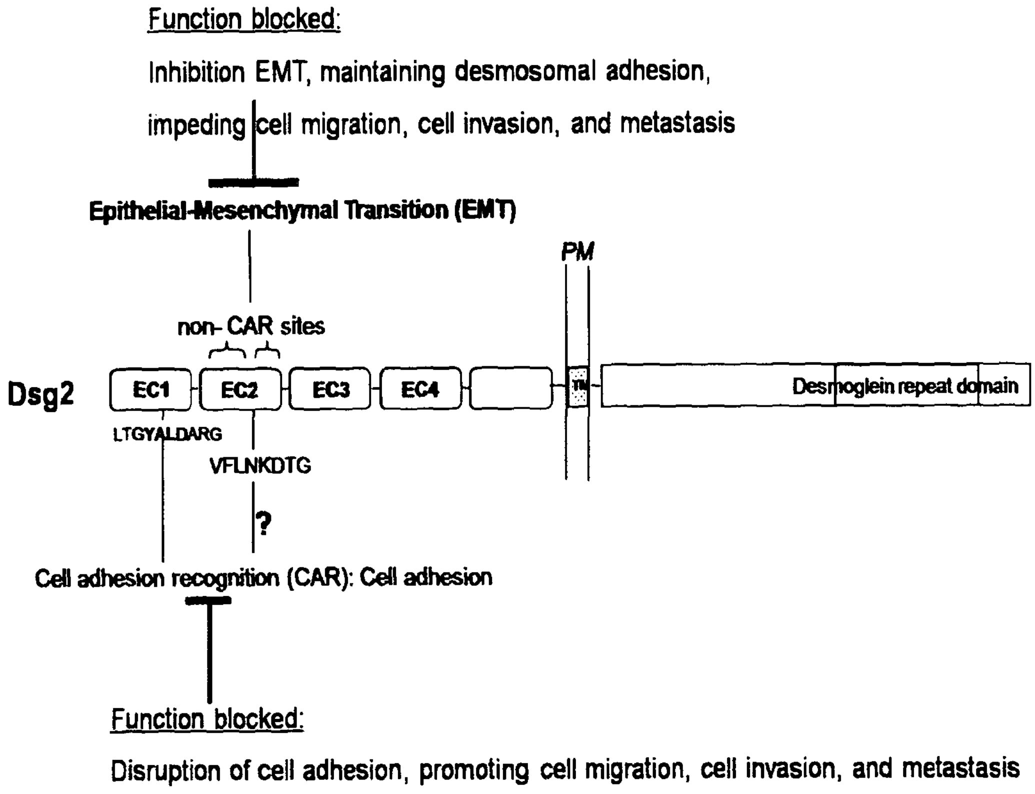

Database UniProt, Nov. 1, 1997, "Q14126 (DSG2_HUMAN)", Database accession No. Q14126.

Database UniProt, Nov. 25, 2002, O55111 (DSG2_MOUSE), Database accession No. O55111.

Davies Eleri Lloyd et al, "The Role of desmoglein 2 and E-cadherin in the invasion and motility of human breast cancer cells", International Journal of Oncology Spandidos Publications GR, 1997, vol. 11, No. 2, pp. 415-419.

Gregory B Lesinski et al, "Bortezomib pre-treatment prolongs interferon-alpha-induced STAT1 phosphorylation in melanoma cells" Cancer Immunology, Immunotherapy, Springer, Berlin, DE, 2009, vol. 58, No. 12, pp. 2031-2037.

Kurrey NK et al, "Snail and Slug are major determinants of ovarian cancer invasiveness at the transcription level", Gynecologic Oncology, Academic Press, London GB, 2005, vol. 97, No. 1, pp. 155-165.

Lorch Jochen H et al, "Bortezomib upregulates the EGF-receptor and inhibits cell-cell adhesion and cell migration in squamous cell cancer of the head and neck", Proceedings of the American Association for Cancer Research Annual Meeting, 2007, vol. 48, pp. 951.

Lu Ming et al, "Targeted inhibition of EG-1 blocks breast tumor growth", Cancer Biology & Therapy, 2007, vol. 6, No. 6, pp. 936-941.

Morris et al, "A Phase II Trial of Bortezomib and Prednisone for Castration Resistant Metastatic Prostate Cancer", Journal of Urology, Lippincott Williams & Wilkins, Baltimore, MD US, 2007, vol. 178, No. 6, pp. 2378-2384.

PCT/GB2010/001776 International Search Report and Written Opinion dated Jan. 14, 2011 (28 pages).

* cited by examiner

Figure 3: page 1
(a) A375 melanoma cells
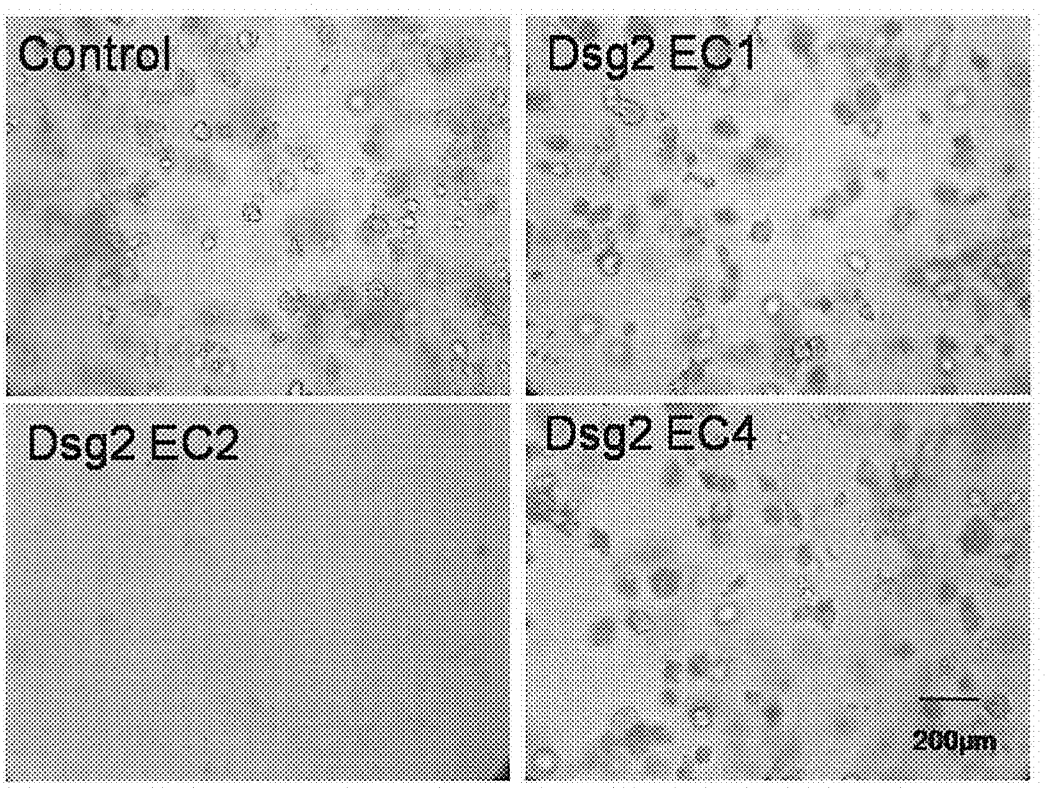

Figure 3: page 2
(b) MCF7 breast cancer cells
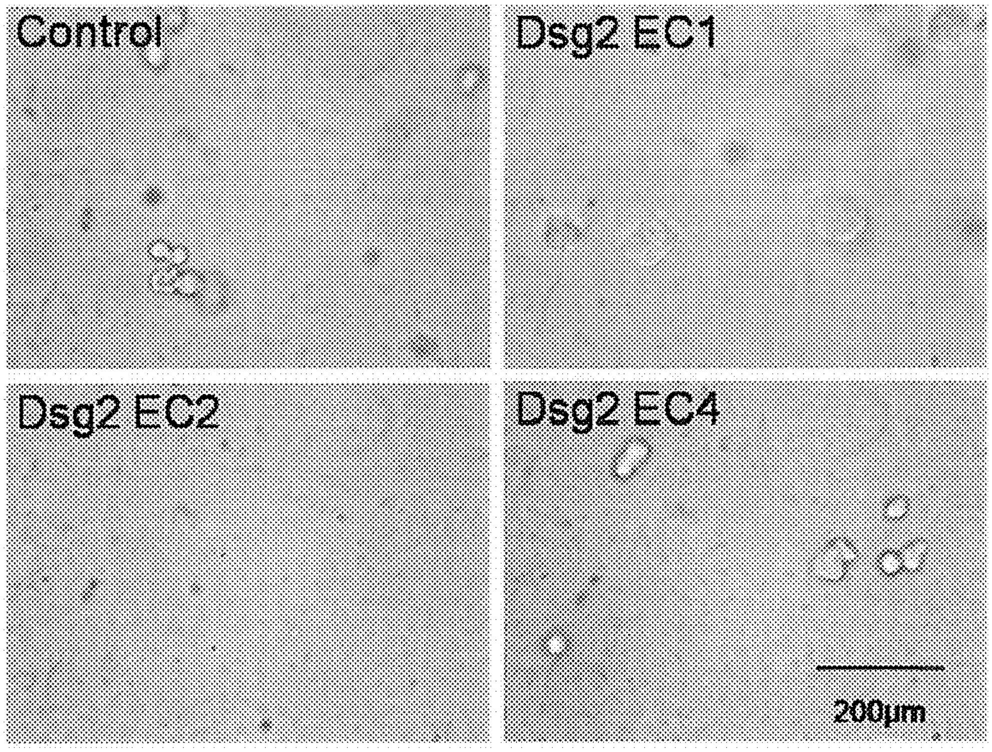

Figure 3: page 3
(c) LNCaP prostate cancer cells
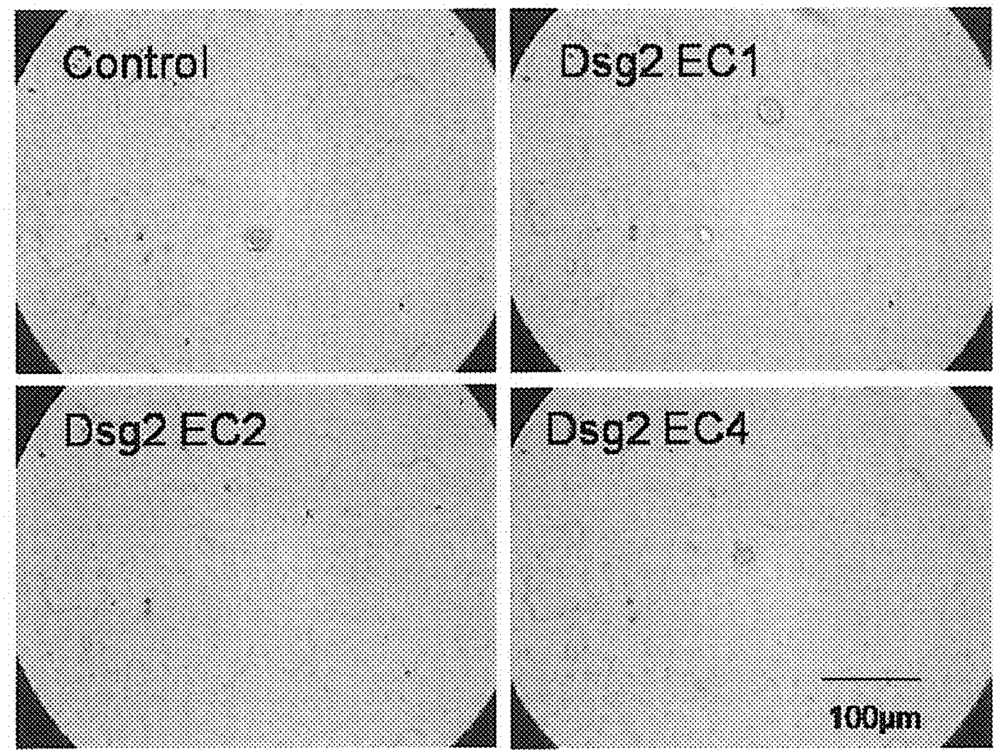

Figure 4
(A) HGF/SF induced EMT on MDCK cells
Control | Anti-non-CAR antibody 25μg/ml
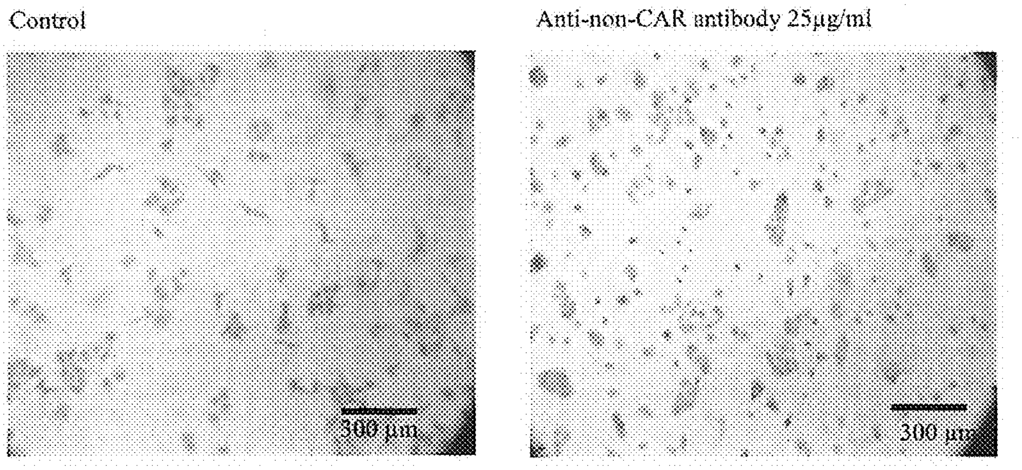
(B) MCF7 breast cancer cell
Control | Anti-non-CAR antibody 50μg/ml
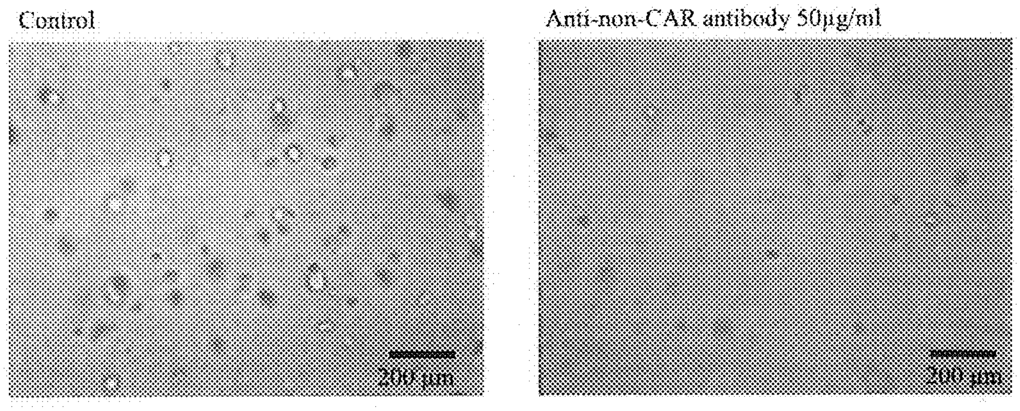

Figure 5: page 1
(A)
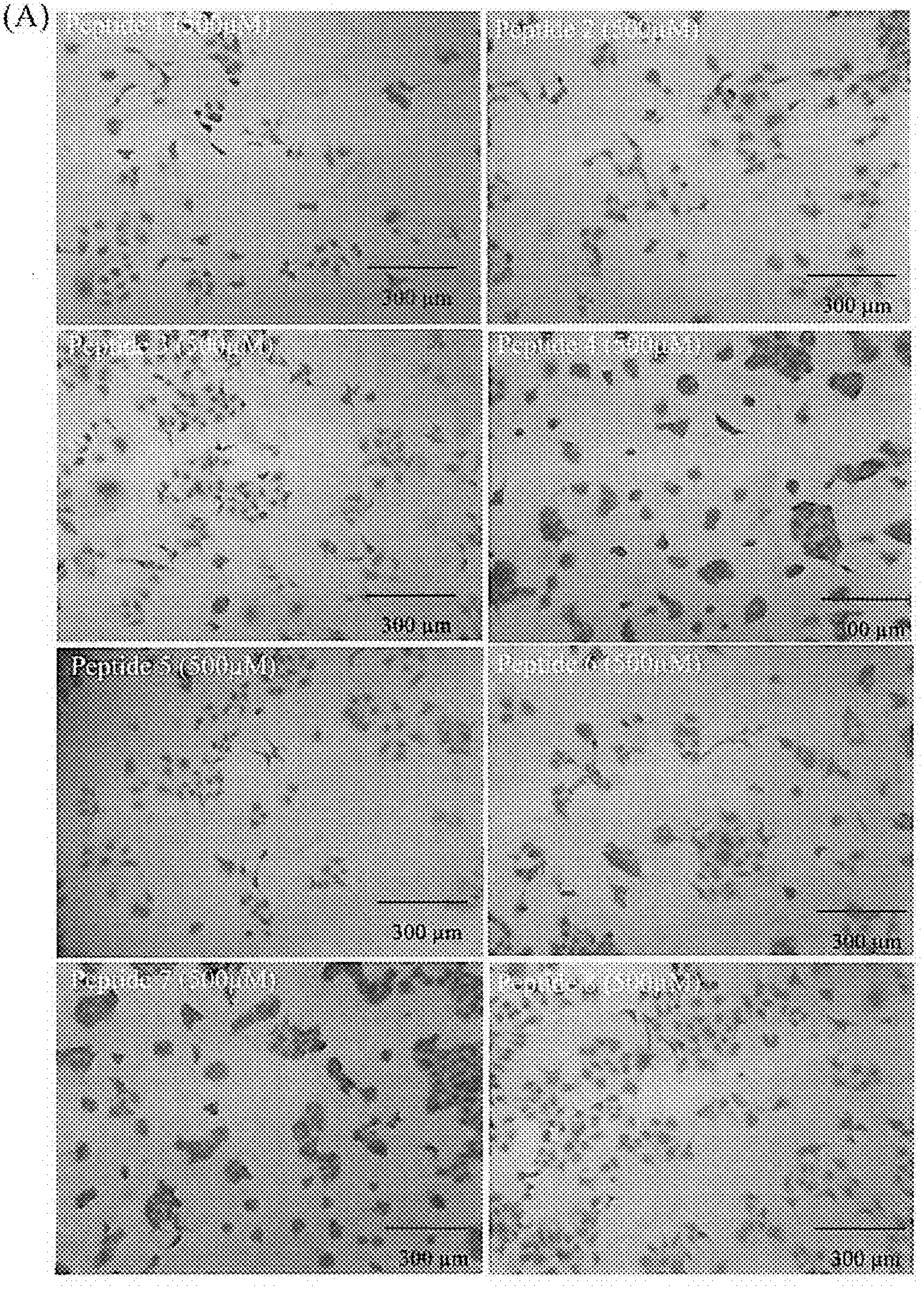

Figure 5: page 2
(B) MCF7 breast cancer cells
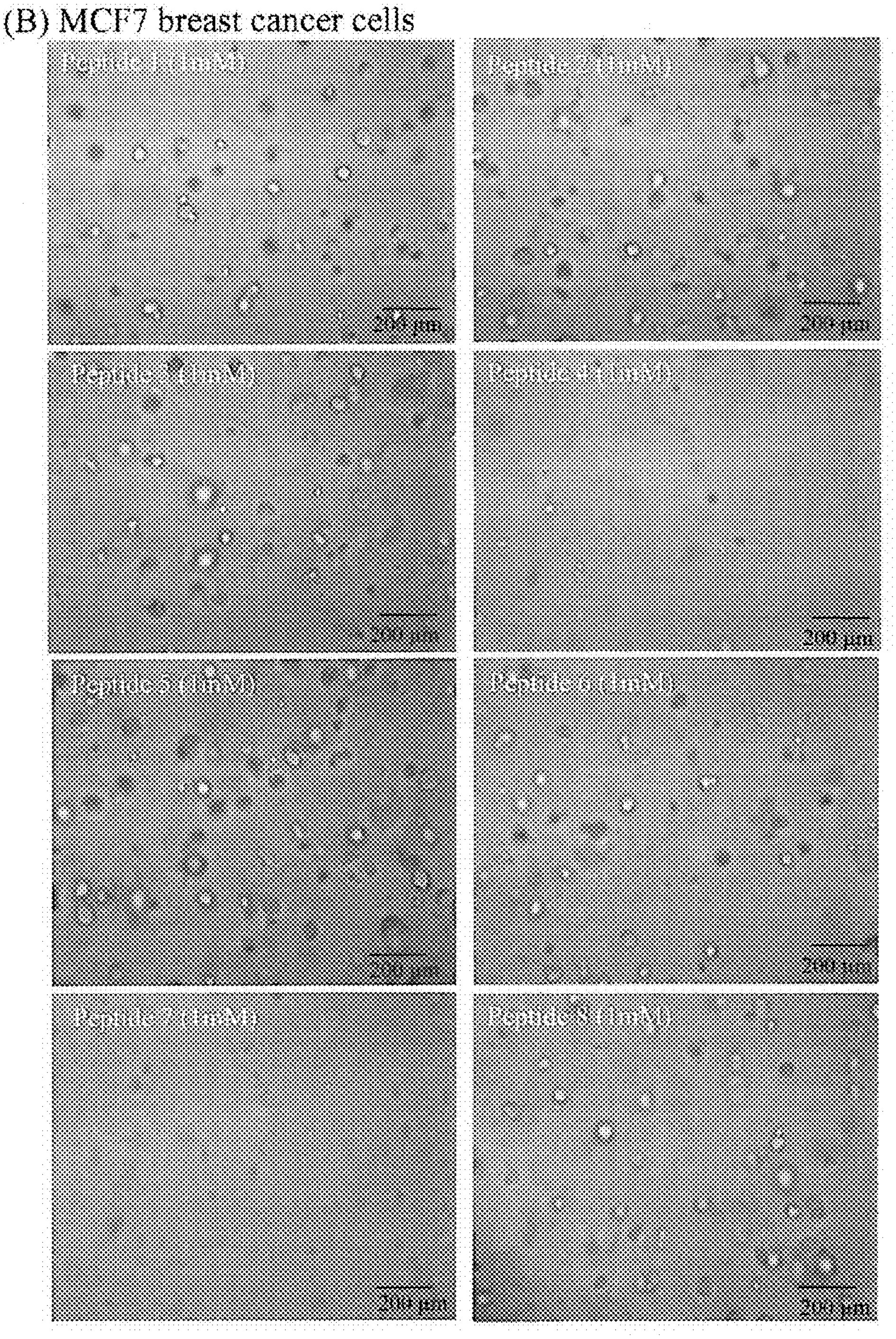

TREATMENT OF CANCER

The present invention relates to agents for use in treating cancer.

Cancer is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

Cancer is caused by both external factors (tobacco, infectious organisms, chemicals, and radiation) and internal factors (inherited mutations, hormones, immune conditions, and mutations that occur from metabolism). These causal factors may act together or in sequence to initiate or promote carcinogenesis. Cancer may affect people at all ages, even fetuses, but the risk for most varieties increases with age. Cancer causes about 13% of all human deaths. According to the American Cancer Society, 7.6 million people died from cancer in the world during 2007. Diagnosis usually requires the histologic examination of a tissue biopsy specimen by a pathologist, although the initial indication of malignancy can be symptoms or radiographic imaging abnormalities.

Nearly all cancers are caused by abnormalities in the genetic material of the transformed cells. These abnormalities may be due to the effects of carcinogens, such as tobacco smoke, radiation, chemicals, or infectious agents. Other cancer-promoting genetic abnormalities may be randomly acquired through errors in DNA replication, or are inherited, and thus present in all cells from birth. The heritability of cancers is usually affected by complex interactions between carcinogens and the host's genome. New aspects of the genetics of cancer pathogenesis, such as DNA methylation, and microRNAs are increasingly recognized as important.

Genetic abnormalities found in cancer typically affect two general classes of genes. Cancer-promoting oncogenes are typically activated in cancer cells, giving those cells new properties, such as hyperactive growth and division, protection against programmed cell death, loss of respect for normal tissue boundaries, and the ability to become established in diverse tissue environments. Tumor suppressor genes are then inactivated in cancer cells, resulting in the loss of normal functions in those cells, such as accurate DNA replication, control over the cell cycle, orientation and adhesion within tissues, and interaction with protective cells of the immune system.

Most cancers can be treated and some cured, depending on the specific type, location, and stage. Once diagnosed, cancer is usually treated with a combination of surgery, chemotherapy and radiotherapy. As research develops, treatments are becoming more specific for different varieties of cancer. There has been significant progress in the development of targeted therapy drugs that act specifically on detectable molecular abnormalities in certain tumors, and which minimize damage to normal cells. The prognosis of cancer patients is most influenced by the type of cancer, as well as the stage, or extent of the disease. In addition, histologic grading and the presence of specific molecular markers can also be useful in establishing prognosis, as well as in determining individual treatments.

Metastasis is the spread of a disease, such as cancer, from one organ or part to another non-adjacent organ or part. Cancer cells can break away, leak, or spill from a primary tumor, enter lymphatic and blood vessels, circulate through the bloodstream, and settle down to grow within normal tissues elsewhere in the body. Metastasis is one of three hallmarks of malignancy (contrast benign tumors). Most tumors and other neoplasms can metastasize, although in varying degrees (e.g., glioma and basal cell carcinoma rarely metastasize). When tumor cells metastasize, the new tumor is called a secondary or metastatic tumor, and its cells are like those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

Treatment and survival is determined by whether or not a cancer is local or has spread to other locations. If the cancer spreads to other tissues and organs, it may decrease a patient's likelihood of survival. However, there are some cancers (i.e., leukemia, cancer of the brain) that can kill without spreading at all. When cancer has metastasized, it may be treated with radiosurgery, chemotherapy, radiation therapy, biological therapy, hormone therapy, surgery or a combination of these. The choice of treatment generally depends on the type of primary cancer, the size and location of the metastasis, the patient's age and general health, and the types of treatments used previously. In patients diagnosed with CUP, it is still possible to treat the disease even when the primary tumor cannot be located. The treatment options currently available are rarely able to cure metastatic cancer.

Against this background, it is clearly desirable to identify new agents that can be used for the treatment of cancer.

Desmosomes are one of the principal types of cell-cell adhesion junction between epithelial, myocardial and other tissues. Such desmosomes contain transmembrane glycoproteins called desmosomal cadherin, desmocollin (Dsc) and desmoglein (Dsg). Each occurs as at least three distinct genetic isoforms that show tissue-specific expression patterns.

Dsg2 are ubiquitously expressed in all tissues that form desmosomes. The extracellular domains of Dsg2 contain four cadherin repeat domains (EC1-4), each about 110 amino acids each in length. The extracellular repeat domain EC1 contains cell adhesion recognition (CAR) sites, which provide cell-cell adhesion. Therefore, Dsg2 has been identified to be a transmembrane cell adhesion molecule. Additionally, recent studies show that Dsg2 is not just a simple cell-cell adhesion molecule. Dsg2 is involved in promotion of angiogenesis, signalling of apoptosis, and is a substrate for MMPs.

The inventors have now determined that Dsg2 has an important role in regulating epithelial-mesenchymal transition (EMT) in cells. EMT is a program of development of cells characterized by loss of cell adhesion and increased cell mobility. EMT is essential for numerous developmental processes including mesoderm formation and neural tube formation. EMT also plays a central role during tumour progression, invasion and metastasis. Cancer cells undergo EMT to lose cell adhesion and acquire mesenchymal characteristics, some of which are necessary for invasion and metastasis.

A first aspect of the invention provides an antagonist of Dsg2 for use as a medicament for preventing or treating cancer, wherein said antagonist modulates the function of the amino acid sequence: TQDVFVGSVEELSAAHTLVMKINATDADEPNTLNSKISYR (SEQ ID NO:1), or a fragment or variant thereof, of the EC2 domain of Dsg2.

As mentioned above, the inventors have determined that Dsg2 has an important role in regulating EMT. They have shown that: (1) Triggering EMT using hepatocyte growth factor/scattering factor (HGF/SF) shows that most of the desmosomal adhesion components are down-regulated, except Dsg2. (2) Epithelial cells transfected with Dsg2 exhibit a mesenchymal-like morphology and showed greater migration and invasion abilities under treatment by HGF/SF. (3) Antibodies against EC2 domain of Dsg2 significantly block HGF/SF-induced EMT in vitro. Furthermore, the inventors have determined that antibodies to the EC2 domain of Dsg2 inhibit invasion of cancer cells, including MCF7 human breast cancer cells, LNCaP human prostate cancer cells, and KM12 human colon cancer cells. While not wishing to be bound to any particular theory, they propose that Dsg2 can function in the cell to promote EMT.

The authors of international patent publication WO 99/57149 suggest that cell adhesion recognition (CAR) sites derived from the EC2 domain of Dsg2 can be used as modulating agents for treating cancer and/or inhibiting metastasis. The authors state that such modulating agents should inhibit cadherin-mediated cell adhesion. Surprisingly, the inventors have determined that the CAR site within the EC2 domain of Dsg2 does not have a function in mediating the EMT promoting activity of Dsg2. In contrast, non-CAR sequences of the EC2 domain of Dsg2 regulate the EMT promoting activity of Dsg2. Peptide fragments derived from non-CAR sequences of the EC2 domain of Dsg2 block EMT and cell invasion in vitro, as do antibodies raised to an EC2 domain of Dsg2 without the CAR sequence. Thus, the inventors have demonstrated that non-CAR sequences of the EC2 domain of Dsg2 regulate the EMT promoting function of Dsg2. Until the present invention, no role has been ascribed to non-CAR sequences present in the EC2 domain of Dsg2. The non-CAR sequences have no homology to the CAR sequences.

Peptide fragments derived from non-CAR sequences of the EC2 domain of Dsg2, and antibodies raised to an EC2 domain of Dsg2 without the CAR sequence, antagonise the EMT promoting function of Dsg2. Therefore, antagonists of the function of the non-CAR sequences of the EC2 domain of Dsg2 clearly have much utility as agents for preventing or treating cancer, particularly by reducing EMT and associated invasion and metastatic potential of cancerous cells. This was not known, and could not have been predicated from, any information previously known concerning Dsg2 and its role in EMT.

Dsg2 (desmoglein2) is a human transmembrane cell adhesion protein. A schematic overview of the protein structure is provided in FIG. 1. An example of an amino acid sequence of Dsg2 is provided at the end of the examples in SEQ ID NO:2; further examples can be located from protein databases, for example NCBI accession NP_001934.2.

The EC2 domain of Dsg2 (extracellular domain 2) is located from amino acid positions 161 to 273 of the sequence provided in SEQ ID NO:2, and is provided below:

```
                                          (SEQ ID NO: 3)
QDVFVGSVEELSAAHTLVMKINATDADEPNTLNSKISYRIVSLEPAYPPV

FYLNKDTGEIYTTSVILDREEHSSYTLTVEARDGNGEVTDKPVKQAQVQI

RILDVNDNIPVVE.
```

The proposed CAR sequence in the EC2 domain of Dsg2 is located from amino acid positions 210 to 218 of the sequence provided in SEQ ID NO:2, and is provided below:

```
                                          (SEQ ID NO: 4)
                 VFYLNKDTG
```

The inventors have identified non-CAR sequences within the EC2 domain of Dsg2 that have a role in regulating the EMT promoting activity of Dsg2. This region is located from amino acid positions 160 to 199 of the sequence provided in SEQ ID NO:2, and is provided below:

```
                                          (SEQ ID NO: 1)
   TQDVFVGSVEELSAAHTLVMKINATDADEPNTLNSKISYR
```

The first aspect of the invention concerns antagonists of Dsg2, in which the antagonist modulates the function of the amino acid sequence: TQDVFVGSVEELSAAHTLVMKINATDADEPNTLNSKISYR (SEQ ID NO:1), or a fragment or variant thereof, of the EC2 domain of Dsg2.

By "the amino acid sequence: TQDVFVGSVEELSAAHTLVMKINATDADEPNTLNSKISYR (SEQ ID NO:1), or a fragment or variant thereof, of the EC2 domain of Dsg2" we include that the antagonist modulates the function of the amino acid sequence of SEQ ID NO:1 to regulate the EMT promoting function of Dsg2. By "a fragment or variant thereof" of SEQ ID NO:1, we include that the antagonist affect part of the EC2 domain defined in SEQ ID NO:1, or variants of that sequence.

A "fragment" of said peptide will preferably comprise less than the total amino acid sequence of the full native peptide; preferably the fragment retains its biological activity: in this case, its ability to regulate the EMT promoting function of Dsg2.

A "variant" of the peptide also refers to a peptide wherein at one or more positions there have been amino acid insertions, deletions, or substitutions, either conservative or non-conservative, provided that such changes result in a protein whose basic properties, for example ability to regulate the EMT promoting function of Dsg2; protein interaction; thermostability; activity in a certain pH-range (pH-stability), have not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis as would be well known to those skilled in the art.

The accompanying examples provide assays that can be readily used by the skilled person to measure the effect of Dsg2 on EMT and cell invasion: the "Blocking EMT assay" and the "Cell invasion assay". As shown by the inventors, these assays can be used to measure the antagonistic potential of agents on Dsg2-mediated EMT and cell invasion.

By "antagonist" we include any substance that interferes with the physiological action of Dsg2 polypeptide; preferably by affecting the EMT promoting function. Preferably the aspects of the invention provide a therapeutically effective amount of the said antagonist. For the purposes of the present specification a "therapeutically effective amount" of an antagonist is an amount of such an antagonist that is sufficient to prevent or treat cancer in a subject to whom the antagonist is administered.

An embodiment of the first aspect of the invention is wherein the antagonist reduces the EMT promoting function of Dsg2; preferably by reducing the function of the amino acid sequence: TQDVFVGSVEELSAAHTLVMKINATDADEPNTLNSKISYR (SEQ ID NO:1), or a fragment or variant thereof, of the EC2 domain of Dsg2. This can be measured as a reduction in the EMT promoting function of Dsg2; preferably the antagonist reduces the function by 10%, 20%, 30%, 40%, 50%, 60%, 70%, 80%, 90%, 95%, 99% or more. The "Blocking EMT assay" and "Cell invasion assay" described in the accompanying examples can be used measure the EMT promoting function of Dsg2, and hence the effect of the antagonist on that activity.

It can be appreciated that there are various ways in which an antagonist can modulate the function of the amino acid sequence: TQDVFVGSVEELSAAHTLVMKINATDADEPNTLNSKISYR (SEQ ID NO:1), or a fragment or variant thereof, of the EC2 domain of Dsg2.

For example, in one embodiment of the invention the antagonist specifically binds the amino acid sequence of SEQ ID NO:1. Such an antagonist can prevent the non-CAR region of EC2 regulating the EMT promoting activity of Dsg2. by "specifically binds to", we include where the antagonist binds to some of the amino acid residues in the amino acid sequence of SEQ ID NO:1, i.e. the antagonist does not have to bind to all the residues to prevent the non-CAR region of EC2 regulating the EMT promoting activity of Dsg2

In a further embodiment of the invention the antagonist includes some or all of the amino acid sequence of SEQ ID NO:1, or amino acid derivatives or analogues thereof. Such an antagonist can be a competitive inhibitor for the function mediated by the non-CAR region of EC2.

A further embodiment of the invention is wherein the antagonist binds to a molecule which the non-CAR region of EC2 interacts with, as part of its function of regulating the EMT promoting activity of Dsg2.

An example of an antagonist would include a chemical ligand that binds to and affects said polypeptide function, and in broader terms this could also include an antibody, or antibody fragment, that binds to one of the said polypeptides such that the polypeptide cannot effect its normal function. The antagonist may also alter the sub-cellular localisation of polypeptide. In this way, the amount of functional polypeptide is reduced.

Preferably, the antagonist of the first aspect of the invention is an antibody or antibody fragment or derivative; a peptide; a peptidomimetic; or a small molecule.

Preferably the antibody is a monoclonal or polyclonal antibody.

The use of antibodies as agents to modulate polypeptide activity is well known. Indeed, therapeutic agents based on antibodies are increasingly being used in medicine, including several different types of cancer. In the accompanying examples, the inventors provide exemplification of polyclonal antibody that can bind to a Dsg2 polypeptide lacking a CAR sequence in EC2; hence this antibody is an antagonist according to the first aspect of the invention.

Antibodies may be produced as polyclonal sera by injecting antigen into animals. Preferred polyclonal antibodies may be raised by inoculating an animal (e.g. a rabbit) with antigen using techniques known to the art.

Polyclonal antibodies, for use in treating human subjects, may be raised against a number of peptides derived from the amino acid sequence of SEQ ID NO:1. For instance, as shown in the accompanying examples, a polyclonal antibody was raised to the sequence: TQDVFVGSVEELSAAHTLVMKINATDADEPNTLNSKISYRIVSLEPAYPPVFYLN KDC (SEQ ID NO:5) which corresponds to part of the Dsg2 EC2 domain without a CAR region.

Alternatively the antibody may be monoclonal. Conventional hybridoma techniques may be used to raise such antibodies. The antigen used to generate monoclonal antibodies for use as antagonists in the present invention may be the same as would be used to generate polyclonal sera; i.e. all or a fragment or variant of TQDVFVGSVEELSAAHTLVMKINATDADEPNTLNSKISYRIVSLEPAYPPVFYLN KDC (SEQ ID NO: 5).

In their simplest form, antibodies or immunoglobulin proteins are Y-shaped molecules usually exemplified by the IgG class of antibodies. The molecule consists of four polypeptide chains two identical heavy (H) chains and two identical (L) chains of approximately 50 kD and 25 kD each respectively. Each light chain is bound to a heavy chain (H-L) by disulphide and non-covalent bonds. Two identical H-L chain combinations are linked to each other by similar non-covalent and disulphide bonds between the two H chains to form the basic four chain immunoglobulin structure $(H\text{-}L)_2$.

Light chain immunoglobulins are made up of one V-domain ($V_L$) and one constant domain ($C_L$) whereas heavy chains consist of one V-domain and, depending on H chain isotype, three or four C-domains ($C_H1$, $C_H2$, $C_H3$ and $C_H4$).

At the N-terminal region of each light or heavy chain is a variable (V) domain that varies greatly in sequence, and is responsible for specific binding to antigen. Antibody specificity for antigen is actually determined by amino acid sequences within the V-regions known as hypervariable loops or Complementarity Determining Regions (CDRs). Each H and L chain V regions possess 3 such CDRs, and it is the combination of all 6 that forms the antibody's antigen binding site. The remaining V-region amino acids which exhibit less variation and which support the hypervariable loops are called frameworks regions (FRs).

The regions beyond the variable domains (C-domains) are relatively constant in sequence. It will be appreciated that the characterising feature of antibodies according to the invention is the $V_H$ and $V_L$ domains. It will be further appreciated that the precise nature of the $C_H$ and $C_L$ domains is not, on the whole, critical to the invention. In fact preferred antibodies for use in the invention may have very different $C_H$ and $C_L$ domains. Furthermore, as discussed more fully below, preferred antibody functional derivatives may comprise the Variable domains without a C-domain (e.g. scFV antibodies).

Preferred antibodies considered to be antagonists of use in the first aspect of the invention may have the $V_L$ (first domain) and $V_H$ (second domain) domains. A derivative thereof may have 75% sequence identity, more preferably 90% sequence identity and most preferably has at least 95% sequence identity. It will be appreciated that most sequence variation may occur in the framework regions (FRs) whereas the sequence of the CDRs of the antibodies, and functional derivatives thereof, should be most conserved.

A number of preferred embodiments of the antagonists of use in the first aspect of the invention relate to molecules with both Variable and Constant domains. However it will be appreciated that antibody fragments (e.g. scFV antibodies or FAbs) are also encompassed by the invention that comprise essentially the Variable region of an antibody without any Constant region.

An scFV antibody fragment considered to be an antagonist of use in the first aspect of the invention may comprise the whole of the $V_H$ and $V_L$ domains of an antibody raised against SEQ ID NO: 1 of Dsg2. The $V_H$ and $V_L$ domains may be separated by a suitable linker peptide.

Antibodies, and particularly mAbs, generated in one species are known to have several serious drawbacks when used to treat a different species. For instance when murine antibodies are used in humans they tend to have a short circulating half-life in serum and may be recognised as foreign proteins by the immune system of a patient being treated. This may lead to the development of an unwanted human anti-mouse antibody (HAMA) response. This is particularly troublesome when frequent administration of an antibody is required as it can enhance its clearance, block its therapeutic effect, and induce hypersensitivity reactions. These factors limit the use of mouse monoclonal antibodies in human therapy and have prompted the development of antibody engineering technology to generate humanised antibodies.

Therefore, where the antibody is to be used as a therapeutic agent for preventing or treating cancer in a human subject, then it is preferred that antibodies and fragments thereof of non-human source are humanised; such antibodies are considered to be antibody derivatives for the purposes of this invention.

Humanisation may be achieved by splicing V region sequences (e.g. from a monoclonal antibody generated in a non-human hybridoma) with C region (and ideally FRs from V region) sequences from human antibodies. The resulting 'engineered' antibodies are less immunogenic in humans than the non-human antibodies from which they were derived and so are better suited for clinical use.

Humanised antibodies may be chimeric monoclonal antibodies, in which, using recombinant DNA technology, rodent immunoglobulin constant regions are replaced by the constant regions of human antibodies. The chimeric H chain and L chain genes may then be cloned into expression vectors containing suitable regulatory elements and induced into mammalian cells in order to produce fully glycosylated antibodies. By choosing an appropriate human H chain C region gene for this process, the biological activity of the antibody may be pre-determined. Such chimeric molecules may be used to treat or prevent glaucoma.

Further humanisation of antibodies may involve CDR-grafting or reshaping of antibodies. Such antibodies are produced by transplanting the heavy and light chain CDRs of a non-human antibody (which form the antibody's antigen binding site) into the corresponding framework regions of a human antibody.

Humanised antibody fragments represent preferred agents for use according to the invention. Human FAbs recognising an epitope on SEQ ID NO:1 may be identified through screening a phage library of variable chain human antibodies. Techniques known to the art (e.g as developed by Morphosys or Cambridge Antibody Technology) may be employed to generate Fabs that may be used as antagonists according to the invention. In brief a human combinatorial Fab antibody library may be generated by transferring the heavy and light chain variable regions from a single-chain Fv library into a Fab display vector. This library may yield $2.1\times10^{10}$ different antibody fragments. The peptide may then be used as "bait" to identify antibody fragments from then library that have the desired binding properties.

Domain antibodies (dAbs) represent another preferred agent that may be used according to this embodiment of the invention. dAbs are the smallest functional binding unit of antibodies and correspond to the variable regions of either the heavy or light chains of human antibodies. Such dAbs may have a molecule weight of around 13 kDa (corresponding to about 1/10 (or less) the size of a full antibody).

Further preferred agents that may be used according to this embodiment of the invention include bispecific Fab-scFv (a "bibody") and trispecific Fab-(scFv)(2) (a "tribody"). For bibodies or tribodies, a scFv molecule is fused to one or both of the VL-CL (L) and VH-$CH_1$ (Fd) chains, e.g., to produce a tribody two scFvs are fused to C-term of Fab while in a bibody one scFv is fused to C-term of Fab. The preparation of such molecules can be routinely performed by the skilled person from information available in the field.

The antagonist can also be a peptide or peptiomimetic, comprising some or all of the amino acid sequence of SEQ ID NO:1, or amino acid derivative or analogues thereof.

In the accompanying examples, the inventors provide exemplification of peptides containing some of the amino acid sequence of SEQ ID NO:1: KINATDADEPNTLNSKISYR (SEQ ID NO:6) and EELSAAHTLV (SEQ ID NO:7). The inventors have demonstrated that the peptides can antagonise the EMT promoting function of Dsg2, and hence they are preferred embodiments of the antagonist of the invention.

In addition to the peptides of SEQ ID NO:6 and SEQ ID NO:7, further peptides can be prepared comprising some of the amino acid sequence of SEQ ID NO:1. The utility of such further peptides as antagonists of the EMT promoting function of Dsg2 can be measured using the "Blocking EMT assay" and the "Cell invasion assay" described in the accompanying examples.

The preparation of peptides is a routine process. For example, the peptides used in the accompanying experiments were synthesized by Peptide 2.0 Inc (Chantilly, Va., USA); many other companies offer the commercial synthesis of peptides. Laboratory techniques are also well known for the preparation of peptides, such methods being readily performed by a skilled person. Hence the skilled person can prepare peptides containing some or all of the amino acid sequence of SEQ ID NO:1, and test their utility as antagonists of the EMT promoting function of Dsg2 using the information provided herein and from common general knowledge.

The peptide antagonists according to the invention may comprise all 40 amino acid residues of SEQ ID NO:1, with or without any amino acid substitutions. However, as mentioned above the inventors have determined that peptides having 10 amino acids (EELSAAHTLV (SEQ ID NO:7)) and 20 amino acids (KINATDADEPNTLNSKISYR (SEQ ID NO:6)) can antagonise the EMT promoting function of Dsg2. Accordingly preferred peptides according to the invention can range from about 10 amino acids (for example, 7, 8, 9, 10, 11 or 12) to around 20 amino acids (for example, 18, 19, 20, 21, 22).

The peptide antagonists can also contain further amino acid sequences which are not derived from the amino acid sequence of SEQ ID NO:1: for example, other amino acid sequences which provide a separate function of the peptide (such as a tag, or a catalytic domain). Such peptides are also included in the antagonists of the invention.

Also, it will be appreciated that the invention may be put into effect using derivatives or analogues of these preferred peptides that still lie within the definition of the amino acid sequence provided by SEQ ID NO:1.

By the term "derivative or analogue thereof", we mean a peptide within which amino acids residues are replaced by residues (whether natural amino acids, non-natural amino acids or amino acid mimics) with similar side chains or peptide backbone properties. Additionally, either one or both terminals of such peptides may be protected by N and C-terminal protecting groups, for example, groups with similar properties to acetyl or amide groups. It will be appreciated that the amino acid sequenced may be varied, truncated or modified once the final peptide is formed. As mentioned above, the skilled person can test a derivative or analogue for utility as antagonists of the EMT promoting function of Dsg2 using the information provided herein and from common general knowledge.

Such derivatives may increase or decrease the peptide half-life in vivo. Examples of derivatives capable of increasing the half-life of peptide and polypeptides according to the invention include peptoid derivatives of the polypeptides, D-amino acid derivatives of the polypeptides, and peptide-peptoid hybrids.

Peptides and polypeptides according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which derivatives that have enhanced stability in biological contexts can be designed and produced. Such polypeptide derivatives may have improved bioavailability as a result of increased resistance to protease-mediated degradation. Preferably, a derivative or analogue suitable for use according to the invention is more protease-resistant than the peptide from which it is derived.

Preferably, the polypeptide may be made more protease-resistant by protecting the N and/or C terminal. For example, the N terminal may be protected by an acetyl group, or by an alkyl or aryl group, or an alkyl-CO— or aryl-CO— group, each of which may be optionally substituted. The C terminal may be protected by an amide group or by a substituted amide group.

Protease-resistance of a polypeptide derivative and the polypeptide from which it is derived may be evaluated by means of well-known protein degradation assays. The relative values of protease resistance for the polypeptide derivative and polypeptide may then be compared.

Peptoid derivatives of the polypeptides of the invention may be readily designed from knowledge of the structure of the polypeptide. Commercially available software may be used to develop peptoid derivatives according to well-established protocols.

Retropeptoids, (in which all amino acids are replaced by peptoid residues in reversed order) are also able to mimic antibacterial polypeptides derived from apolipoproteins. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of peptides according to the invention comprises D-amino acid forms of the peptide. The preparation of peptides using D-amino acids rather than L-amino acids greatly decreases any unwanted breakdown of such an agent by normal metabolic processes, decreasing the amounts of agent which need to be administered, along with the frequency of its administration.

The peptides, analogues, or derivatives of the invention represent products that may advantageously be expressed by biological cells.

The term "peptidomimetic" refers to a compound that mimics the conformation and desirable features of a particular peptide as a therapeutic agent, but that avoids the undesirable features. For example, morphine is a compound which can be orally administered, and which is a peptidomimetic of the peptide endorphin. There are a number of different approaches to the design and synthesis of peptidomimetics, as is well known in the art.

The antagonist of the invention may also be a small molecule. The term "small molecule" is well known in pharmacology and biochemistry as a low molecular weight chemical compound. Many pharmaceutical drugs are small molecules. Such antagonists may be identified as part of a high throughput screen of small molecule libraries. The screening method according to the invention (see below) represents a suitable means of identifying such inhibitors.

Further types of antagonist molecules are also included within the first aspect of the invention. For example, the antagonist may be an aptamer.

Aptamers are nucleic acid molecules that assume a specific, sequence-dependent shape and bind to specific target ligands based on a lock-and-key fit between the aptamer and ligand. Typically, aptamers may comprise either single- or double-stranded DNA molecules (ssDNA or dsDNA) or single-stranded RNA molecules (ssRNA). Aptamers may be used to bind both nucleic acid and non-nucleic acid targets. Accordingly aptamers may be generated that recognise and so bind to and modulate the function of function of the amino acid sequence: TQDVFVGSVEELSAAHTLVMKINATDADEPNTLNSKISYR (SEQ ID NO:1), or a fragment or variant thereof, of the EC2 domain of Dsg2. Suitable aptamers may be selected from random sequence pools, from which specific aptamers may be identified which bind to the selected target molecules with high affinity. Methods for the production and selection of aptamers having desired specificity are well known to those skilled in the art, and include the SELEX (systematic evolution of ligands by exponential enrichment) process. Briefly, large libraries of oligonucleotides are produced, allowing the isolation of large amounts of functional nucleic acids, by an iterative process of in vitro selection and subsequent amplification through polymerase chain reaction.

A second aspect of the invention provides an antagonist of Dsg2 for use as a medicament for preventing or treating cancer, wherein said antagonist is a Dsg2 polypeptide or a fragment or variant thereof, wherein said polypeptide has one or more amino acid residue substitutions, inversion and/or deletions within the sequence TQDVFVGSVEELSAAHTLVMKINATDADEPNTLNSKISYR (SEQ ID NO:1) or a fragment or variant thereof, of the EC2 domain of Dsg2.

As well as antagonists which affect the EMT promoting function of Dsg2 by modulating the function of the amino acid sequence: TQDVFVGSVEELSAAHTLVMKINATDADEPNTLNSKISYR (SEQ ID NO:1), another type of antagonist of use in the invention can be a Dsg2 polypeptide in which the amino acid sequence of (SEQ ID NO:1) is altered so as to be non-functional. Such a polypeptide can act as an antagonist by functioning as a competitive inhibitor of native Dsg2, and hence reduce the EMT promoting function of native Dsg2.

Until the present invention, it was not known and was not obvious that the amino acid region of SEQ ID NO:1 regulated the EMT promoting function of Dsg2.

As mentioned above, the skilled person can test whether a Dsg2 polypeptide having one or more amino acid residue replacements, inversion and/or deletions within the sequence TQDVFVGSVEELSAAHTLVMKINATDADEPNTLNSKISYR (SEQ ID NO:1) has utility as antagonists of the EMT promoting function of Dsg2 using the "Blocking EMT assay" and "Cell invasion assay" described in the accompanying examples.

The polypeptide of this aspect of the invention can comprise SEQ ID NO:2 or a fragment thereof wherein said polypeptide has one or more amino acid residue substitutions, inversion and/or deletions within the sequence TQDVFVGSVEELSAAHTLVMKINATDADEPNTLNSKISYR (SEQ ID NO:1). By "fragment" we include where the polypeptide does not include all of the amino acid sequence of Dsg2, but can function as an antagonist of the EMT promoting function of Dsg2.

A "variant" of the polypeptide refers to Dsg2 polypeptide wherein at one or more positions there have been amino acid insertions, deletions, or substitutions, either conservative or non-conservative. For example, the polypeptide may contain deletions of some or all of the amino acid residues of SEQ ID NO:1.

Methods of preparing a polypeptide of the second aspect of the invention are well known in the art; for example using recombinant DNA technologies as set out in Sambrook et al (2001): Molecular cloning, a laboratory manual, $3^{nd}$ edition, Cold Spring Harbor Press, Cold Spring Harbor, N.Y.

An example of an amino acid sequence of Dsg2 is provided at the end of the examples in SEQ ID NO:2; further examples can be located from protein databases, for example NCBI accession number NP_001934.2. An example of a nucleic acid sequence encoding an amino acid sequence of Dsg2 can be found at NCBI accession number NG_007072.2.

From this information, the skilled person can readily prepare a Dsg2 polypeptide having one or more amino acid residue replacements, inversion and/or deletions within the sequence TQDVFVGSVEELSAAHTLVMKINATDADEPNTLNSKISYR (SEQ ID NO:1).

A preferred embodiment of the second aspect of the invention is wherein the antagonist is a polypeptide comprising the amino acid sequence of SEQ ID NO:8. SEQ ID NO: 8 is provided at the end of the examples below. The polypeptide sequence of SEQ ID NO:8 corresponds to a Dsg2 polypeptide having the amino acid sequence of SEQ ID NO:2, but without the non-CAR sequence of EC2, as set out in SEQ ID NO:4.

A preferred embodiment of the second aspect of the invention is wherein the antagonist is a polypeptide comprising the amino acid sequence of SEQ ID NO:9. SEQ ID NO: 9 is provided at the end of the examples below. The polypeptide sequence of SEQ ID NO:9 corresponds to a Dsg2 polypeptide having the amino acid sequence of SEQ ID NO:2, but without the EC 1 and EC2 CAR sequences.

A third aspect of the invention provides an antagonist of the EMT promoting function of Dsg2 for use as a medicament for preventing or treating cancer.

As mentioned above, the authors of international patent publication WO 99/57149 suggest that cell adhesion recognition (CAR) sites derived from the EC2 domain of Dsg2 can be used as modulating agents for treating cancer and/or inhibiting metastasis. The authors state that such modulating agents should inhibit cadherin-mediated cell adhesion.

However, we wish to point out that modulating agents derived from the CAR site of the EC2 domain of Dsg2 do not function as antagonists of the EMT promoting function of Dsg2. This can be clearly seen from the data presented in the accompanying examples. Hence the modulating agents disclosed in WO 99/57149 are not antagonists of the third aspect of the invention.

Moreover, until the present invention, it was not known and was not obvious which region of the Dsg2 polypeptide was responsible for regulating the EMT promoting function of Dsg2.

By "antagonists of the EMT promoting function of Dsg2", we include those antagonists discussed above in relation to the first and second aspects of the invention; i.e. where the antagonist specifically binds the amino acid sequence of SEQ ID NO:1; where the antagonist includes some or all of the amino acid sequence of SEQ ID NO:1, or amino acid derivatives or analogues thereof; where the antagonist binds to a molecule which the non-CAR region of EC2 interacts with, as part of its function of regulating the EMT promoting activity of Dsg2.

Preferably, the antagonist of this aspect of the invention is an antibody or antibody fragment or derivative; a peptide; a peptidomimetic; or a small molecule. Preferably, the antagonist of this aspect of the invention is a monoclonal or polyclonal antibody; or a peptide or peptiomimetic, comprising some or all of the amino acid sequence of SEQ ID NO:1, or amino acid derivative or analogues thereof; for example a peptides comprising the amino acid sequence of KINATDADEPNTLNSKISYR (SEQ ID NO:6) and EELSAAHTLV (SEQ ID NO:7).

Preferably, the antagonist of this aspect of the invention is a Dsg2 polypeptide or a fragment or variant thereof, wherein said polypeptide has one or more amino acid residue substitutions, inversion and/or deletions within the sequence TQDVFVGSVEELSAAHTLVMKINATDADEPNTLNSKISYR (SEQ ID NO:1) or a fragment or variant thereof, of the EC2 domain of Dsg2; preferably the antagonist is a polypeptide comprising the amino acid sequence of SEQ ID NO:8; preferably the antagonist is a polypeptide comprising the amino acid sequence of SEQ ID NO:9.

The utility of further agents as antagonists of the EMT promoting function of Dsg2 can be measured using the "Blocking EMT assay" and the "Cell invasion assay" described in the accompanying examples. For example, the antagonist may be identified according to the screening method according to the invention.

As discussed above, the antagonists of the aspects of the invention may function to reduce the EMT promoting function of Dsg2. EMT is a program of development of cells characterized by loss of cell adhesion and increased cell mobility. EMT encompasses a number of different developmental processes. Those most relevant to the function of Dsg2 in cancer include cell metastasis and cell invasion. Therefore, preferably the antagonists of the aspects of the invention reduce the cell metastasis and/or cell invasion promoting function of Dsg2. Methods of determining the effect of an antagonist on the cell metastasis and/or cell invasion promoting function of Dsg2 are provided herein in the "Blocking EMT assay" and the "Cell invasion assay" described in the accompanying examples.

By "cancer" we include all types of cancer; for example, bladder; breast (female and male); colon; rectal; endometrial; kidney (renal cell); leukemias; lung; melanoma; Non-Hodgkin lymphoma; pancreatic; prostate; skin; and thyroid.

In the accompanying examples the inventors have demonstrated the EMT promoting function of Dsg2 in prostate cancer, breast cancer and skin cancer cell lines. Hence a preferred embodiment of the invention is wherein said cancer is prostate cancer, breast cancer or skin cancer.

The antagonists of the first, second and third aspects of the invention are used to prevent or treat cancer.

Methods of diagnosing cancer are well known in the art; see, for example, www.cancer.gov, which provides details of different types of cancer; how they are diagnosed; and potential treatments.

The antagonists of the first, second and third aspects of the invention are used as medicaments. Various means by which the medicaments can be formulated are provided below.

A further aspect of the invention provide the use of an antagonist according to the first, second or third aspect of the invention in the manufacture of a medicament for preventing or treating cancer.

A still further aspect of the invention provides a method of treating cancer comprising administering to a subject a therapeutically effective quantity of an antagonist according to the first, second or third aspect of the invention.

A fourth aspect of the invention provides a peptide comprising the amino acid sequence TQDVFVGSVEELSAAHTLVMKINATDADEPNTLNSKISYR (SEQ ID NO:1), KINATDADEPNTLNSKISYR (SEQ ID NO:6) or EELSAAHTLV (SEQ ID NO:7), or a fragment or variant thereof.

Until the present invention, it was not known and was not obvious which region of the Dsg2 polypeptide was responsible for regulating the EMT promoting function of Dsg2. Hence the peptides of this aspect of the invention could not have been expected to have utility as antagonists of the EMT promoting function of Dsg2.

Preferably the peptide of this aspect of the invention is an antagonist of Dsg2, which modulates the function of the amino acid sequence: TQDVFVGSVEELSAAHTLVMKINATDADEPNTLNSKISYR (SEQ ID NO:1), or a fragment or variant thereof, of the EC2 domain of Dsg2. By "fragment or variant thereof" we include those fragments or variants of the peptide discussed above in relation to the first aspect of the invention.

Further information concerning the preparation of a peptide according to this aspect of the invention may be found at, for example, the first aspect of the invention given above. Also, the example provides details as to how a peptide of this aspect of the invention can be prepared.

A fifth aspect of the invention provides a polypeptide comprising the amino acid sequence of SEQ ID NO:2 or a fragment or variant thereof, wherein said polypeptide has one or more amino acid residue replacements, inversions and/or deletions within the sequence TQDVFVGSVEELSAAHTLVMKINATDADEPNTLNSKISYR (SEQ ID NO: 1) or a fragment or variant thereof, of the EC2 domain of Dsg2.

An embodiment of this aspect of the invention is wherein the polypeptide comprises the amino acid sequence of SEQ ID NO:8 or SEQ ID NO:9.

Until the present invention, it was not known and was not obvious which region of the Dsg2 polypeptide was responsible for regulating the EMT promoting function of Dsg2.

Hence the polypeptide of this aspect of the invention could not have been expected to have utility as antagonists of the EMT promoting function of Dsg2.

Preferably the polypeptide of this aspect of the invention is an antagonist of Dsg2. By "fragment or variant thereof" we include those fragments or variants of the polypeptide discussed above in relation to the second aspect of the invention.

Further information concerning the preparation of a polypeptide according to this aspect of the invention may be found at, for example, the second aspect of the invention given above. Also, the example provides details as to how a polypeptide of this aspect of the invention can be prepared.

A sixth aspect of the invention provides an antibody capable of specifically binding to the amino acid sequence TQDVFVGSVEELSAAHTLVMKINATDADEPNTLNSKISYR (SEQ ID NO:1) KINATDADEPNTLNSKISYR (SEQ ID NO:6) or EELSAAHTLV (SEQ ID NO:7), or a fragment or variant thereof.

Until the present invention, it was not known and was not obvious which region of the Dsg2 polypeptide was responsible for regulating the EMT promoting function of Dsg2. Hence the antibodies of this aspect of the invention could not have been expected to have utility as antagonists of the EMT promoting function of Dsg2.

Preferably the antibody of this aspect of the invention is an antagonist of Dsg2, which modulates the function of the amino acid sequence: TQDVFVGSVEELSAAHTLVMKINATDADEPNTLNSKISYR (SEQ ID NO:1), or a fragment or variant thereof, of the EC2 domain of Dsg2. By "fragment or variant thereof" we include those fragments or variants of the polypeptide discussed above in relation to the first aspect of the invention.

Further information concerning the preparation of an antibody according to this aspect of the invention may be found at, for example, the first aspect of the invention given above. Also, the example provides details as to how an antibody of this aspect of the invention can be prepared.

A seventh aspect of the invention provides a peptide, polypeptide or antibody of any of the fourth, fifth or sixth aspects of the invention for use in medicine.

An eighth aspect of the invention provides a pharmaceutical composition comprising a therapeutically effective amount of an antagonist, peptide, polypeptide or antibody according to the invention and optionally a pharmaceutically acceptable vehicle. In one embodiment, the amount of the antagonist, peptide, polypeptide or antibody is an amount from about 0.01 mg to about 800 mg. In another embodiment, the amount of the antagonist, peptide, polypeptide or antibody is an amount from about 0.01 mg to about 500 mg. In another embodiment, the amount of the antagonist, peptide, polypeptide or antibody is an amount from about 0.01 mg to about 250 mg. In another embodiment, the amount of the antagonist, peptide, polypeptide or antibody is an amount from about 0.1 mg to about 60 mg. In another embodiment, the amount of the antagonist, peptide, polypeptide or antibody is an amount from about 0.1 mg to about 20 mg.

This invention provides a process for making a pharmaceutical composition comprising combining a therapeutically effective amount of an antagonist, peptide, polypeptide or antibody according to the invention and a pharmaceutically acceptable vehicle. A "therapeutically effective amount" is any amount of an antagonist, peptide, polypeptide or antibody according to the invention which, when administered to a subject provides prevention and/or treatment of cancer. A "subject" is a vertebrate, mammal, domestic animal or human being.

A "pharmaceutically acceptable vehicle" as referred to herein is any physiological vehicle known to those of ordinary skill in the art useful in formulating pharmaceutical compositions.

There are a number of different ways in which the antagonists for use in the invention can be used as a medicament.

The antagonists may be combined in compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the antagonist to the target cell, tissue, or organ. Hence, it is preferred that that antagonist is delivered by means of a suitably protected carrier particle, for example, a micelle.

The antibodies, or functional derivatives thereof, may be used in a number of ways. For instance, systemic administration may be required in which case the antibodies or derivatives thereof may be contained within a composition which may, for example, be ingested orally in the form of a tablet, capsule or liquid. It is preferred that the antibodies, or derivatives thereof, are administered by injection into the blood stream. Injections may be intravenous (bolus or infusion) or subcutaneous (bolus or infusion). Alternatively the antibodies may be injected directly to the liver.

Polypeptide therapeutic entities may be combined in pharmaceutical compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the therapeutic to the target cell, tissue, or organ.

In a preferred embodiment, the pharmaceutical vehicle is a liquid and the pharmaceutical composition is in the form of a solution. In another embodiment, the pharmaceutical vehicle is a gel and the composition is in the form of a cream or the like.

Antagonists may also be incorporated within a slow or delayed release device. Such devices may, for example, be inserted on or under the skin, and the compound may be released over weeks or even months. Such devices may be particularly advantageous when long term treatment with an antagonist according to the invention is required and which would normally require frequent administration (e.g. at least daily injection).

It will be appreciated that the amount of an antagonist that is required is determined by its biological activity and bioavailability which in turn depends on the mode of administration, the physicochemical properties of the antagonist employed, and whether the antagonist is being used as a monotherapy or in a combined therapy. Also, the amount will be determined by the number and state of target cells to be treated. The frequency of administration will also be influenced by the above-mentioned factors and particularly the half-life of the antagonist within the subject being treated.

Optimal dosages to be administered may be determined by those skilled in the art, and will vary with the particular antagonist in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of antagonist according to the invention and precise therapeutic regimes (such as daily doses of the antagonist and the frequency of administration).

Generally, a daily dose of between 0.01 µg/kg of body weight and 0.5 g/kg of body weight of antagonist according to the invention may be used for the prevention and/or treatment of cancer, depending upon which specific antagonist is used. More preferably, the daily dose is between 0.01 mg/kg of body weight and 200 mg/kg of body weight, and most preferably, between approximately 1 mg/kg and 100 mg/kg.

Daily doses may be given as a single administration (e.g. a single daily injection). Alternatively, the antagonist used may require administration twice or more times during a day. As an example, an antagonist according to the invention may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

A ninth aspect of the invention provides a method of screening for antagonists of Dsg2, wherein said antagonist modulates the function of the amino acid sequence: TQDVFVGSVEELSAAHTLVMKINATDADEANTLNSKISYR (SEQ ID NO:1), or a fragment or variant thereof, of the EC2 domain of Dsg2, comprising (i) exposing a cell having a Dsg2 polypeptide to a test compound; (ii) and the effect of the test compound on the function of the amino acid sequence of SEQ ID NO:1 of the EC2 domain of Dsg2 is determined.

The method of the invention can be used to identify compounds which may be of use in treating cancer.

An embodiment of the ninth aspect of the invention is wherein the method further comprises the step of selecting a test compound that reduces the EMT promoting activity of Dsg2.

An embodiment of the ninth aspect of the invention is wherein the method further comprises the step of mixing the selected agent (or a derivative or analogue thereof) with a pharmaceutically acceptable carrier.

The methods of the ninth aspect of the invention relate to screening methods for drugs or lead compounds. The test compound may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The methods of the seventh and eighth aspects of the invention include a step of determining the effect of the test compound on the function of the amino acid sequence of SEQ ID NO:1 of the EC2 domain of Dsg2.

In common with all these methods is the need for a "reference sample", i.e. a sample of protein or nucleic acid taken from an animal or cell which has not been exposed to the test compound. By comparing the function the amino acid sequence of SEQ ID NO:1 of the EC2 domain of Dsg2 in a sample of protein or nucleic acid taken from an animal or cell which has not been exposed to the test compound, to the function of the amino acid sequence of SEQ ID NO:1 of the EC2 domain of Dsg2 in a sample of protein or nucleic acid taken from an animal or cell which has been exposed to the test compound it is possible to determine the effect of the test compound on the function of the amino acid sequence of SEQ ID NO:1 of the EC2 domain of Dsg2. This will show the test compound(s) to produce a potentiation, inhibition or no effect on the function of the amino acid, sequence of SEQ ID NO:1 of the EC2 domain of Dsg2.

The step of assessing the function of the amino acid sequence of SEQ ID NO:1 of the EC2 domain of Dsg2 may be performed using a number of different methods.

The screening methods of the invention can be used in "library screening" methods, a term well known to those skilled in the art. Thus, for example, the methods of the invention may be used to detect (and optionally identify) a test compound capable of affecting the function of the amino acid sequence of SEQ ID NO:1 of the EC2 domain of Dsg2. Aliquots of a library may be tested for the ability to give the required result.

A further embodiment of the method of the seventh and eighth aspects of the invention is wherein the selected compound is formulated into a pharmaceutically acceptable composition.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The invention will now be further described with reference to the following examples and Figures.

FIG. 1: The difference in functional blocking between CAR and non-CAR sites.

Figure 2:
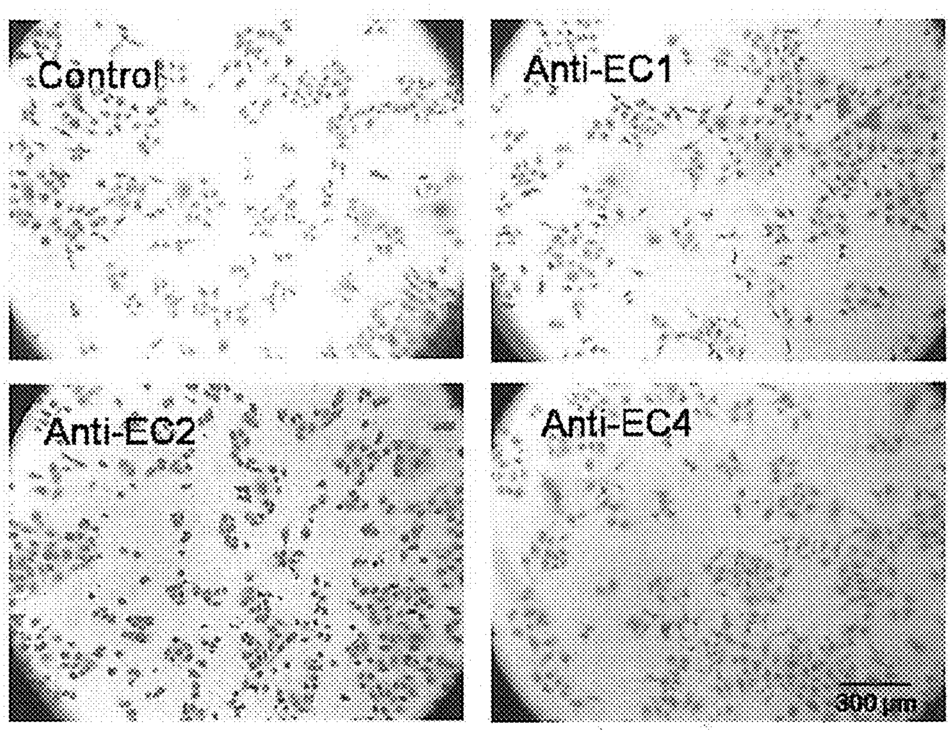

FIG. 2: Anti-Dsg2 EC2 antibodies inhibit EMT. Anti-EC1 and anti-EC4 antibodies don't inhibit EMT.

FIG. 3: Anti-Dsg2 EC2 antibodies inhibit the invasion abilities of (A) human melanoma A375 cells, (B) human breast cancer MCF7 cells, and (C) human prostate cancer LNCaP cells.

FIG. 4: Dsg2 EC2 peptide sequences without its full CAR domain (VFYLNKDTGE)(SEQ ID NO:4)were used to generate a rabbit polyclonal antibody. (A) EMT is significantly inhibited by the antibodies generated; (B) The cell invasion assay measures the ability of cells to grow and penetrate a gel made of 'Matrigel'. The antibodies generated inhibit the invasion abilities of human breast cancer MCF7 cells.

FIG. 5: 8 synthetic peptides were prepared. (A) EMT is significantly blocked by the non-CAR sequences of Dsg2 EC2, Peptides 4 and 7; whereas the CAR sequences and other non-CAR sequences do not affect EMT. (B) The cell invasion ability of human breast cancer MCF7 cells has been inhibited by the non-CAR sequences, Peptides 4 and 7.

EXAMPLE 1

Determining the Function of Dsg2 for Regulating Epithelial-Mesenchymal Transition Introduction The present invention concerns inhibition of epithelial-mesenchymal transition (EMT) by modulating the function of non-CAR sequences of the EC2 domain of Dsg2.

Desmosomes are one of the principal types of cell-cell adhesion junction between epithelial, myocardial and other tissues. Such desmosomes contain transmembrane glycoproteins called desmosomal cadherin, desmocollin (Dsc) and desmoglein (Dsg). Each occurs as at least three distinct genetic isoforms that show tissue-specific expression patterns.

Dsg2 is ubiquitously expressed in all tissues that form desmosomes. The extracellular domains of Dsg2 contain four cadherin repeat domains (EC1-4) about 110 amino acids each in length. The extracellular repeat domain EC1 contains cell adhesion recognition (CAR) sites, which provide cell-cell adhesion. Therefore, Dsg2 has been identified to be a transmembrane cell adhesion molecule. However, very recent studies show that Dsg2 is not just a simple cell-cell adhesion molecule. Dsg2 is involved in promotion of angiogenesis, signalling of apoptosis, and is a substrate for MMPs. Moreover, it has previously been determined that Dsg2 can play a role in EMT. EMT is a very different physiological action to cell-cell adhesion.

Against this background, the inventors investigated the role of Dsg2 and specific regions within that protein in regulating EMT, and whether Dsg2 could be modulated to inhibit cancer cell invasion.

Results and Discussion

It has previously been suggested that Dsg2 has a role in EMT. However it is not known how this activity of Dsg2 is mediated.

FIG. 1 presents a schematic diagram of Dsg2, along with known and proposed functions of domains within that protein. The extracellular repeat domain EC1 and EC2 contains cell adhesion recognition (CAR) sites, which provide cell-cell adhesion. The cell adhesion function of Dsg2 CAR sequence (LTGYALDARG; SEQ ID NO: 10) in EC1 domain is known, and it has been proposed that a CAR sequence (VFYLNKDTGE; SEQ ID NO: 4) in EC2 domain has a similar function in cell adhesion.

The inventors studied the effect of antibodies that specifically bind to the EC1, EC2 and EC4 domains of Dsg2 on EMT. As can be seen in FIGS. 2 and 3, Anti-EC2 antibodies inhibit EMT and inhibit cell invasion of human melanoma, breast cancer and prostate cancer cells, while anti-EC1 and anti-EC4 antibodies do not have such an effect. Hence it seems that the EMT regulating activity of Dsg2 is mediated by sequences within the EC2 domain of that protein.

The EC2 domain of Dsg2 has been proposed to contain a CAR domain. CAR domains in Dsg2 and other desmocollin (Dsc) and desmoglein proteins (Dsc1, Dsc2, Dsc3, Dsg1, Dsg2, and Dsg3) have previously been demonstrated to have function in cell adhesion. However, it is known that blocking desmosomal adhesion via CAR promotes cell migration, cell invasion, and metastasis. In contrast anti-EC2 antibodies inhibit EMT, resulting in maintaining cell adhesion and impeding cell migration, cell invasion, and metastasis. Hence it seems unlikely that a CAR sequence in the EC2 domain of Dsg2 is responsible for any EMT-promoting activity of that protein.

Accordingly, the inventors decided to locate the region of the EC2 domain of Dsg2 which regulates the EMT promoting activity of that protein. To do so, the inventors generated a rabbit polyclonal antibody to peptide derived from Dsg2 EC2, but lacking the full CAR domain:

```
                                        (SEQ ID NO: 5)
TQDVFVGSVEELSAAHTLVMKINATDADEPNTLNSK1SYRIVSLEPAYPP

VFYLNKDC.
```

The antibodies were then used in a "blocking EMT assay" and "cell invasion assay" (details below) to determine their effect on cells. The results are shown in FIG. 4. It can be seen that EMT is significantly inhibited by the antibodies generated (panel A), and also that the antibodies generated inhibit the invasion abilities of human breast cancer MCF7 cells (panel B). Hence this data clearly shows that the EMT promoting function of Dsg2 is mediated by a non-CAR region in EC2.

The inventors then prepared a series of peptides derived from the EC2 domain of Dsg2:

```
Peptide 1:
                                      (SEQ ID NO: 11)
Control Peptide             (YTRLGANLAG).

Peptide 2:
                                      (SEQ ID NO: 10)
CAR Sequence of EC1         (LTGYALDARG).

Peptide 3:
                                       (SEQ ID NO: 4)
CAR Sequence of EC2         (VFYLNKDTGE).

Peptide 4:
                                       (SEQ ID NO: 6)
non-CAR Sequence of EC2     (KINATDADEPNTLNSKISYR).

Peptide 5:
                                      (SEQ ID NO: 12)
non-CAR Sequence of EC2     (YTTSVTLDREEHSSY).

Peptide 6:
                                      (SEQ ID NO: 13)
non-CAR Sequence of EC2     (ARDGNGEVTDKPVKQ).

Peptide 7:
                                       (SEQ ID NO: 7)
non-CAR Sequence of EC2     (EELSAAHTLV).

Peptide 8:
                                      (SEQ ID NO: 14)
non-CAR Sequence of EC2     (IVSLEPAYPP).
```

The peptides were then used in a "blocking EMT assay" and "cell invasion assay" (details below) to determine their effect on cells. The results are shown in FIG. 5. It can be seen that EMT and cell invasion is significantly inhibited by peptides 4 and 7. Again this data clearly shows that the EMT promoting function of Dsg2 is mediated by a non-CAR region in EC2.

Hence the inventors have demonstrated that inhibition and antagonists of the non-CAR sequences present in EC2 of Dsg2 can block EMT and invasion in vitro, and have the potential to block cancer invasion and metastasis in vivo.

Experimental Protocols

Generation of the Antibodies: The polyclonal antibodies were generated by Abgent (San Diego, Calif., USA). In brief, the immunizing peptide sequence (TQDVFVGSVEEL-SAAHTLVMKINATDADEPNTLNSKISYR-IVSLEPAYPPVFYLN KDC; SEQ ID NO:5) was synthesized, conjugated with a carrier protein KLH (Keyhole Limpet Hemocyanin) and used in immunization of rabbits. The rabbits were bled and the antibodies were prepared by saturated ammonium sulfate precipitation followed by dialysis against PBS.

Peptides: The peptides used in the experiments were synthesized by Peptide 2.0 Inc (Chantilly, Va., USA). Peptide 1: Control Peptide (YTRLGANLAG; SEQ ID NO:11). Peptide 2: CAR sequence of EC1 (LTGYALDARG; SEQ ID NO:10). Peptide 3: CAR sequence of EC2 (VFYLNKDTGE; SEQ ID NO:4). Peptide 4: non-CAR sequence of EC2 (KINATDADEPNTLNSKISYR; SEQ ID NO:6). Peptide 5: non-CAR sequence of EC2 (YTTSVTLDREEHSSY; SEQ ID NO:12). Peptide 6: non-CAR sequence of EC2 (ARDGNGEVTDKPVKQ; SEQ ID NO:13). Peptide 7: non-CAR sequence of EC2 (EELSAAHTLV; SEQ ID NO: 7). Peptide 8: non-CAR sequence of EC2 (IVSLEPAYPP; SEQ ID NO:14).

Blocking EMT Assay: Antibodies or peptides were added to 10% sub-confluent MDCK cells cultured in standard medium with 2.5 ng/ml HGF/SF in 96-well plates for 24 h. EMT was induced by HGF/SF in MDCK cells without any antibody or peptide treatment. The effects of different antibodies and peptides in blocking EMT were investigated by adding different concentrations of them to 10% sub-confluent MDCK cells cultured in standard medium with 2.5 ng/ml HGF/SF.

Cell Invasion Assay: Growth Factor-Reduced Matrigel™ Matrix (BD, Becton Dickinson Biosciences, Bedford, Mass., USA) was thawed in the fridge one day prior to its use. The Matrigel matrix was mixed by pre-cooled pipettes to homogeneity on ice. Four μl of the cell suspension (1×106 cells/ml) in standard medium without (Control) or with 1 μl different concentrations of antibody or peptide was mixed with 95 μl of Matrigel matrix in a cold Eppendorf tube. After thorough mixing using cooled pipettes, 30 μl of the cells in the Matrigel mixture was added to 48-well plates. The plates were incubated at 37° C. in a CO2 incubator for 1 h to polymerize the droplet mixtures. 250 μl of standard medium was added to cover the cell/Matrigel droplet and incubated for several days. Blindly-selected cell invasion images were recorded in four areas within a cell/Matrigel droplet by a Nikon 4500 Coolpix digital camera under the microscope.

```
Sequence listing
Non-CAR sequence of EC2 of Dsg2
                                                       (SEQ ID NO: 1)
TQDVFVGSVEELSAAHTLVMKINATDADEPNTLNSKISYR

Human Dsg2:
                                                       (SEQ ID NO: 2)
marspgraya llllicfnv gsglhlqvls trnenkllpk hphlvrqkra witapvalre

gedlskknpi akihsdlaee rglkitykyt gkgiteppfg ifvfnkdtge lnvtsildre

etpfflltgy aldargnnve kplelrikvl dindnepvft qdvfvgsvee lsaahtlvmk

inatdadepn tlnskisyri vslepayppv fylnkdtgei yttsvtldre ehssytltve

ardgngevtd kpvkqaqvqi rildvndnip vvenkvlegm veenqvnvev trikvfdade

igsdnwlanf tfasgneggy fhietdaqtn egivtlikev dyeemknldf svivankaaf

hksirskykp tpipikvkvk nvkegihfks svisiyvses mdrsskgqii gnfqafdedt

glpaharyvk ledrdnwisv dsvtseikla klpdfesryv qngtytvkiv aisedyprkt

itgtvlinve dindncptli epvqtichda eyvnvtaedl dghpnsgpfs fsvidkppgm
```

-continued aekwkiarqe stsvllqqse kklgrseiqf lisdnqgfsc pekqvltltv ceclhgsgcr
eaqhdsyvgl gpaaialmil aflllllvpl lllmchcgkg akgftpipgt iemlhpwnne
gappedkvvp sflpvdqggs lvgrngvggm akeatmkgss sasivkgqhe msemdgrwee
hrsllsgrat qftgatgaim ttettktara tgasrdmaga qaaavalnee flrnyftdka
asyteedenh takdcllvys qeeteslnas igccsfiege lddrflddlg lkfktlaevc
lgqkidinke ieqrqkpate tsmntashsl ceqtmvnsen tyssgssfpv pkslqeanae
kvtqeivter syssrqaqkv atplpdpmas rnviatetsy vtgstmpptt vilgpsqpqs
livtervyap astlvdqpya negtvvvter viqphgggsn plegtqhlqd vpyvmvrere
sflapssgvq ptlampniav gqnvtvterv lapastlqss yqiptensmt arnttvsgag
vpgplpdfgl eesghsnsti ttsstrvtkh stvqhsys EC2 domain of Dsg2

(SEQ ID NO: 3)

QDVFVGSVEELSAAHTLVMKINATDADEPNTLNSKISYRIVSLEPAYPPVFYLNKDTGEIYTTSVTLDREE
HSSYTLTVEARDGNGEVTDKPVKQAQVQIRILDVNDNIPVVE

CAR sequence of EC2 of Dsg2

(SEQ ID NO: 4)

VFYLNKDTGE

Dsg2 EC2 domain without a CAR sequence (SEQ ID NO: 5)

TQDVFVGSVEELSAAHTLVMKINATDADEPNTLNSKISYRIVSLEPAYPPVFYLNKDC

Fragment of non-CAR sequence of EC2 of Dsg2

(SEQ ID NO: 6)

KINATDADEPNTLNSKISYR

Fragment of non-CAR sequence of EC2 of Dsg2

(SEQ ID NO: 7)

EELSAAHTLV

Human Dsg2 without the non-CAR region of EC2:

(SEQ ID NO: 8)

marspgraya lllllicfnv gsglhlqvls trnenkllpk hphlvrqkra witapvalre
gedlskknpi akihsdlaee rglkitykyt gkgiteppfg ifvfnkdtge lnvtsildre
etpfflltgy aldargnnve kplelrikvl dindnepvfi vslepayppv fylnkdtgei
yttsvtldre ehssytltve ardgngevtd kpvkqaqvqi rildvndnip vvenkvlegm
veenqvnvev trikvfdade igsdnwlanf tfasgneggy fhietdaqtn egivtlikev
dyeemknldf svivankaaf hksirskykp tpipikvkvk nvkegihfks svisiyvses
mdrsskgqii gnfqafdedt glpaharyvk ledrdnwisv dsvtseikla klpdfesryv
qngtytvkiv aisedyprkt itgtvlinve dindncptli epvqtichda eyvnvtaedl
dghpnsgpfs fsvidkppgm aekwkiarqe stsvllqqse kklgrseiqf lisdnqgfsc
pekqvltltv ceclhgsgcr eaqhdsyvgl gpaaialmil aflllllvpl lllmchcgkg
akgftpipgt iemlhpwnne gappedkvvp sflpvdqggs lvgrngvggm akeatmkgss
sasivkgqhe msemdgrwee hrsllsgrat qftgatgaim ttettktara tgasrdmaga
qaaavalnee flrnyftdka asyteedenh takdcllvys qeeteslnas igccsfiege
lddrflddlg lkfktlaevc lgqkidinke ieqrqkpate tsmntashsl ceqtmvnsen
tyssgssfpv pkslqeanae kvtqeivter syssrqaqkv atplpdpmas rnviatetsy
vtgstmpptt vilgpsqpqs livtervyap astlvdqpya negtvvvter viqphgggsn
plegtqhlqd vpyvmvrere sflapssgvq ptlampniav gqnvtvterv lapastlqss -continued yqiptensmt arnttvsgag vpgplpdfgl eesghsnsti ttsstrvtkh stvqhsys Dsg2 without EC1 and EC2 CAR sequence (SEQ ID NO: 9)

marspgraya lllllicfnv gsglhlqvls trnenkllpk hphlvrqkra witapvalre gedlskknpi akihsdlaee rglkitykyt gkgiteppfg ifvfnkdtge lnvtsildre etpffl nnve kplelrikvl dindnepvft qdvfvgsvee lsaahtlvmk inatdadepn tlnskisyri vslepayppi yttsvtldre ehssytltve ardgngevtd kpvkqaqvqi rildvndnip vvenkvlegm veenqvnvev trikvfdade igsdnwlanf tfasgneggy fhietdaqtn egivtlikev dyeemknldf svivankaaf hksirskykp tpipikvkvk nvkegihfks svisiyvses mdrsskgqii gnfqafdedt glpaharyvk ledrdnwisv dsvtseikla klpdfesryv qngtytvkiv aisedyprkt itgtvlinve dindncptli epvqtichda eyvnvtaedl dghpnsgpfs fsvidkppgm aekwkiarqe stsvllqqse kklgrseiqf lisdnqgfsc pekqvltltv ceclhgsgcr eaqhdsyvgl gpaaialmil aflllllvpl lllmchcgkg akgftpipgt iemlhpwnne gappedkvvp sflpvdqggs lvgrngvggm akeatmkgss sasivkgqhe msemdgrwee hrsllsgrat qftgatgaim ttettktara tgasrdmaga qaaavalnee flrnyftdka asyteedenh takdcllvys qeeteslnas igccsfiege lddrflddlg lkfktlaevc lgqkidinke ieqrqkpate tsmntashsl ceqtmvnsen tyssgssfpv pkslqeanae kvtqeivter svssrqaqkv atplpdpmas rnviatetsy vtgstmpptt vilgpsqpqs livtervyap astlvdqpya negtvvvter viqphgggsn plegtqhlqd vpyvmvrere sflapssgvq ptlampniav gqnvtvterv lapastlqss yqiptensmt arnttvsgag vpgplpdfgl eesghsnsti ttsstrvtkh stvqhsys CAR sequence of EC1 of Dsg2

(SEQ ID NO: 10)

LTGYALDARG

Control peptide sequence (SEQ ID NO: 11)

YTRLGANLAG

Fragment of non-CAR sequence of EC2 of Dsg2

(SEQ ID NO: 12)

YTTSVTLDREEHSSY

Fragment of non-CAR sequence of EC2 of Dsg2

(SEQ ID NO: 13)

ARDGNGEVTDKPVKQ

Fragment of non-CAR sequence of EC2 of Dsg2

(SEQ ID NO: 14)

IVSLEPAYPP

---

The invention claimed is:

1. A method of treating cancer comprising administering to a subject having cancer a therapeutically effective quantity of an antagonist of desmoglein 2 (Dsg2), wherein said antagonist is an antibody or antibody fragment that specifically binds to the amino acid sequence: TQDVFVGSVEELSAAHTLVMKINATDADEPNTLNSKISYR (SEQ ID NO: 1), or a biologically active fragment thereof, of the non-cell adhesion recognition (non-CAR) sequence of the EC2 domain of Dsg2, and wherein said antagonist reduces the epithelial-mesenchymal transition (EMT) promoting function of Dsg2.

2. The method of claim 1 wherein said antibody is a polyclonal antibody.

3. The method of claim 1, wherein said antagonist reduces the cell metastasis and/or cell invasion promoting function of Dsg2.

4. The method of claim 1 wherein said cancer is prostate cancer, breast cancer or skin cancer.

5. A method of treating cancer comprising administering to a subject having cancer a therapeutically effective quantity of an antagonist of the epithelial-mesenchymal transition (EMT) promoting function of desmoglein 2 (Dsg2), wherein said antagonist is an antibody or antibody fragment that specifically binds to the amino acid sequence of SEQ ID NO: 1.

* * * * *

SEQUENCE LISTING

<160> NUMBER OF SEQ ID NOS: 14

<210> SEQ ID NO 1
<211> LENGTH: 40
<212> TYPE: PRT
<213> ORGANISM: Homo sapiens

<400> SEQUENCE: 1

Thr Gln Asp Val Phe Val Gly Ser Val Glu Glu Leu Ser Ala Ala His
1 5 10 15

```
Thr Leu Val Met Lys Ile Asn Ala Thr Asp Ala Asp Glu Pro Asn Thr
            20                  25                  30

Leu Asn Ser Lys Ile Ser Tyr Arg
        35                  40


<210> SEQ ID NO 2
<211> LENGTH: 1118
<212> TYPE: PRT
<213> ORGANISM: Homo sapiens

<400> SEQUENCE: 2

Met Ala Arg Ser Pro Gly Arg Ala Tyr Ala Leu Leu Leu Leu Leu Ile
1               5                   10                  15

Cys Phe Asn Val Gly Ser Gly Leu His Leu Gln Val Leu Ser Thr Arg
            20                  25                  30

Asn Glu Asn Lys Leu Leu Pro Lys His Pro His Leu Val Arg Gln Lys
        35                  40                  45

Arg Ala Trp Ile Thr Ala Pro Val Ala Leu Arg Glu Gly Glu Asp Leu
    50                  55                  60

Ser Lys Lys Asn Pro Ile Ala Lys Ile His Ser Asp Leu Ala Glu Glu
65                  70                  75                  80

Arg Gly Leu Lys Ile Thr Tyr Lys Tyr Thr Gly Lys Gly Ile Thr Glu
                85                  90                  95

Pro Pro Phe Gly Ile Phe Val Phe Asn Lys Asp Thr Gly Glu Leu Asn
            100                 105                 110

Val Thr Ser Ile Leu Asp Arg Glu Glu Thr Pro Phe Phe Leu Leu Thr
        115                 120                 125

Gly Tyr Ala Leu Asp Ala Arg Gly Asn Asn Val Glu Lys Pro Leu Glu
    130                 135                 140

Leu Arg Ile Lys Val Leu Asp Ile Asn Asp Asn Glu Pro Val Phe Thr
145                 150                 155                 160

Gln Asp Val Phe Val Gly Ser Val Glu Glu Leu Ser Ala Ala His Thr
                165                 170                 175

Leu Val Met Lys Ile Asn Ala Thr Asp Ala Asp Glu Pro Asn Thr Leu
            180                 185                 190

Asn Ser Lys Ile Ser Tyr Arg Ile Val Ser Leu Glu Pro Ala Tyr Pro
        195                 200                 205

Pro Val Phe Tyr Leu Asn Lys Asp Thr Gly Glu Ile Tyr Thr Thr Ser
    210                 215                 220

Val Thr Leu Asp Arg Glu Glu His Ser Ser Tyr Thr Leu Thr Val Glu
225                 230                 235                 240

Ala Arg Asp Gly Asn Gly Glu Val Thr Asp Lys Pro Val Lys Gln Ala
                245                 250                 255

Gln Val Gln Ile Arg Ile Leu Asp Val Asn Asp Asn Ile Pro Val Val
            260                 265                 270

Glu Asn Lys Val Leu Glu Gly Met Val Glu Glu Asn Gln Val Asn Val
        275                 280                 285

Glu Val Thr Arg Ile Lys Val Phe Asp Ala Asp Glu Ile Gly Ser Asp
    290                 295                 300

Asn Trp Leu Ala Asn Phe Thr Phe Ala Ser Gly Asn Glu Gly Gly Tyr
305                 310                 315                 320

Phe His Ile Glu Thr Asp Ala Gln Thr Asn Glu Gly Ile Val Thr Leu
                325                 330                 335

Ile Lys Glu Val Asp Tyr Glu Glu Met Lys Asn Leu Asp Phe Ser Val
            340                 345                 350
```

-continued

```
Ile Val Ala Asn Lys Ala Ala Phe His Lys Ser Ile Arg Ser Lys Tyr
        355                 360                 365

Lys Pro Thr Pro Ile Pro Ile Lys Val Lys Val Lys Asn Val Lys Glu
    370                 375                 380

Gly Ile His Phe Lys Ser Ser Val Ile Ser Ile Tyr Val Ser Glu Ser
385                 390                 395                 400

Met Asp Arg Ser Ser Lys Gly Gln Ile Ile Gly Asn Phe Gln Ala Phe
                405                 410                 415

Asp Glu Asp Thr Gly Leu Pro Ala His Ala Arg Tyr Val Lys Leu Glu
            420                 425                 430

Asp Arg Asp Asn Trp Ile Ser Val Asp Ser Val Thr Ser Glu Ile Lys
        435                 440                 445

Leu Ala Lys Leu Pro Asp Phe Glu Ser Arg Tyr Val Gln Asn Gly Thr
    450                 455                 460

Tyr Thr Val Lys Ile Val Ala Ile Ser Glu Asp Tyr Pro Arg Lys Thr
465                 470                 475                 480

Ile Thr Gly Thr Val Leu Ile Asn Val Glu Asp Ile Asn Asp Asn Cys
                485                 490                 495

Pro Thr Leu Ile Glu Pro Val Gln Thr Ile Cys His Asp Ala Glu Tyr
            500                 505                 510

Val Asn Val Thr Ala Glu Asp Leu Asp Gly His Pro Asn Ser Gly Pro
        515                 520                 525

Phe Ser Phe Ser Val Ile Asp Lys Pro Pro Gly Met Ala Glu Lys Trp
    530                 535                 540

Lys Ile Ala Arg Gln Glu Ser Thr Ser Val Leu Leu Gln Gln Ser Glu
545                 550                 555                 560

Lys Lys Leu Gly Arg Ser Glu Ile Gln Phe Leu Ile Ser Asp Asn Gln
                565                 570                 575

Gly Phe Ser Cys Pro Glu Lys Gln Val Leu Thr Leu Thr Val Cys Glu
            580                 585                 590

Cys Leu His Gly Ser Gly Cys Arg Glu Ala Gln His Asp Ser Tyr Val
        595                 600                 605

Gly Leu Gly Pro Ala Ala Ile Ala Leu Met Ile Leu Ala Phe Leu Leu
    610                 615                 620

Leu Leu Leu Val Pro Leu Leu Leu Leu Met Cys His Cys Gly Lys Gly
625                 630                 635                 640

Ala Lys Gly Phe Thr Pro Ile Pro Gly Thr Ile Glu Met Leu His Pro
                645                 650                 655

Trp Asn Asn Glu Gly Ala Pro Pro Glu Asp Lys Val Val Pro Ser Phe
            660                 665                 670

Leu Pro Val Asp Gln Gly Gly Ser Leu Val Gly Arg Asn Gly Val Gly
        675                 680                 685

Gly Met Ala Lys Glu Ala Thr Met Lys Gly Ser Ser Ser Ala Ser Ile
    690                 695                 700

Val Lys Gly Gln His Glu Met Ser Glu Met Asp Gly Arg Trp Glu Glu
705                 710                 715                 720

His Arg Ser Leu Leu Ser Gly Arg Ala Thr Gln Phe Thr Gly Ala Thr
                725                 730                 735

Gly Ala Ile Met Thr Thr Glu Thr Thr Lys Thr Ala Arg Ala Thr Gly
            740                 745                 750

Ala Ser Arg Asp Met Ala Gly Ala Gln Ala Ala Ala Val Ala Leu Asn
        755                 760                 765
```

```
Glu Glu Phe Leu Arg Asn Tyr Phe Thr Asp Lys Ala Ala Ser Tyr Thr
    770                 775                 780

Glu Glu Asp Glu Asn His Thr Ala Lys Asp Cys Leu Leu Val Tyr Ser
785                 790                 795                 800

Gln Glu Glu Thr Glu Ser Leu Asn Ala Ser Ile Gly Cys Cys Ser Phe
                805                 810                 815

Ile Glu Gly Glu Leu Asp Asp Arg Phe Leu Asp Asp Leu Gly Leu Lys
            820                 825                 830

Phe Lys Thr Leu Ala Glu Val Cys Leu Gly Gln Lys Ile Asp Ile Asn
        835                 840                 845

Lys Glu Ile Glu Gln Arg Gln Lys Pro Ala Thr Glu Thr Ser Met Asn
    850                 855                 860

Thr Ala Ser His Ser Leu Cys Glu Gln Thr Met Val Asn Ser Glu Asn
865                 870                 875                 880

Thr Tyr Ser Ser Gly Ser Ser Phe Pro Val Pro Lys Ser Leu Gln Glu
                885                 890                 895

Ala Asn Ala Glu Lys Val Thr Gln Glu Ile Val Thr Glu Arg Ser Val
            900                 905                 910

Ser Ser Arg Gln Ala Gln Lys Val Ala Thr Pro Leu Pro Asp Pro Met
        915                 920                 925

Ala Ser Arg Asn Val Ile Ala Thr Glu Thr Ser Tyr Val Thr Gly Ser
    930                 935                 940

Thr Met Pro Pro Thr Thr Val Ile Leu Gly Pro Ser Gln Pro Gln Ser
945                 950                 955                 960

Leu Ile Val Thr Glu Arg Val Tyr Ala Pro Ala Ser Thr Leu Val Asp
                965                 970                 975

Gln Pro Tyr Ala Asn Glu Gly Thr Val Val Val Thr Glu Arg Val Ile
            980                 985                 990

Gln Pro His Gly Gly Gly Ser Asn  Pro Leu Glu Gly Thr  Gln His Leu
        995                 1000                1005

Gln Asp  Val Pro Tyr Val Met  Val Arg Glu Arg Glu  Ser Phe Leu
    1010                 1015                 1020

Ala Pro  Ser Ser Gly Val Gln  Pro Thr Leu Ala Met  Pro Asn Ile
    1025                 1030                 1035

Ala Val  Gly Gln Asn Val Thr  Val Thr Glu Arg Val  Leu Ala Pro
    1040                 1045                 1050

Ala Ser  Thr Leu Gln Ser Ser  Tyr Gln Ile Pro Thr  Glu Asn Ser
    1055                 1060                 1065

Met Thr  Ala Arg Asn Thr Thr  Val Ser Gly Ala Gly  Val Pro Gly
    1070                 1075                 1080

Pro Leu  Pro Asp Phe Gly Leu  Glu Glu Ser Gly His  Ser Asn Ser
    1085                 1090                 1095

Thr Ile  Thr Thr Ser Ser Thr  Arg Val Thr Lys His  Ser Thr Val
    1100                 1105                 1110

Gln His  Ser Tyr Ser
    1115


<210> SEQ ID NO 3
<211> LENGTH: 113
<212> TYPE: PRT
<213> ORGANISM: Homo sapiens

<400> SEQUENCE: 3

Gln Asp Val Phe Val Gly Ser Val Glu Glu Leu Ser Ala Ala His Thr
1               5                   10                  15
```

-continued

Leu Val Met Lys Ile Asn Ala Thr Asp Ala Asp Glu Pro Asn Thr Leu
20 25 30

Asn Ser Lys Ile Ser Tyr Arg Ile Val Ser Leu Glu Pro Ala Tyr Pro
35 40 45

Pro Val Phe Tyr Leu Asn Lys Asp Thr Gly Glu Ile Tyr Thr Thr Ser
50 55 60

Val Thr Leu Asp Arg Glu Glu His Ser Ser Tyr Thr Leu Thr Val Glu
65 70 75 80

Ala Arg Asp Gly Asn Gly Glu Val Thr Asp Lys Pro Val Lys Gln Ala
85 90 95

Gln Val Gln Ile Arg Ile Leu Asp Val Asn Asp Asn Ile Pro Val Val
100 105 110

Glu

<210> SEQ ID NO 4
<211> LENGTH: 10
<212> TYPE: PRT
<213> ORGANISM: Homo sapiens

<400> SEQUENCE: 4

Val Phe Tyr Leu Asn Lys Asp Thr Gly Glu
1 5 10

<210> SEQ ID NO 5
<211> LENGTH: 58
<212> TYPE: PRT
<213> ORGANISM: Homo sapiens

<400> SEQUENCE: 5

Thr Gln Asp Val Phe Val Gly Ser Val Glu Glu Leu Ser Ala Ala His
1 5 10 15

Thr Leu Val Met Lys Ile Asn Ala Thr Asp Ala Asp Glu Pro Asn Thr
20 25 30

Leu Asn Ser Lys Ile Ser Tyr Arg Ile Val Ser Leu Glu Pro Ala Tyr
35 40 45

Pro Pro Val Phe Tyr Leu Asn Lys Asp Cys
50 55

<210> SEQ ID NO 6
<211> LENGTH: 20
<212> TYPE: PRT
<213> ORGANISM: Homo sapiens

<400> SEQUENCE: 6

Lys Ile Asn Ala Thr Asp Ala Asp Glu Pro Asn Thr Leu Asn Ser Lys
1 5 10 15

Ile Ser Tyr Arg
20

<210> SEQ ID NO 7
<211> LENGTH: 10
<212> TYPE: PRT
<213> ORGANISM: Homo sapiens

<400> SEQUENCE: 7

Glu Glu Leu Ser Ala Ala His Thr Leu Val
1 5 10

<210> SEQ ID NO 8

<211> LENGTH: 1078
<212> TYPE: PRT
<213> ORGANISM: Homo sapiens

<400> SEQUENCE: 8

Met Ala Arg Ser Pro Gly Arg Ala Tyr Ala Leu Leu Leu Leu Leu Ile
1               5                   10                  15

Cys Phe Asn Val Gly Ser Gly Leu His Leu Gln Val Leu Ser Thr Arg
            20                  25                  30

Asn Glu Asn Lys Leu Leu Pro Lys His Pro His Leu Val Arg Gln Lys
        35                  40                  45

Arg Ala Trp Ile Thr Ala Pro Val Ala Leu Arg Glu Gly Glu Asp Leu
    50                  55                  60

Ser Lys Lys Asn Pro Ile Ala Lys Ile His Ser Asp Leu Ala Glu Glu
65                  70                  75                  80

Arg Gly Leu Lys Ile Thr Tyr Lys Tyr Thr Gly Lys Gly Ile Thr Glu
                85                  90                  95

Pro Pro Phe Gly Ile Phe Val Phe Asn Lys Asp Thr Gly Glu Leu Asn
            100                 105                 110

Val Thr Ser Ile Leu Asp Arg Glu Glu Thr Pro Phe Phe Leu Leu Thr
        115                 120                 125

Gly Tyr Ala Leu Asp Ala Arg Gly Asn Asn Val Glu Lys Pro Leu Glu
    130                 135                 140

Leu Arg Ile Lys Val Leu Asp Ile Asn Asp Asn Glu Pro Val Phe Ile
145                 150                 155                 160

Val Ser Leu Glu Pro Ala Tyr Pro Pro Val Phe Tyr Leu Asn Lys Asp
                165                 170                 175

Thr Gly Glu Ile Tyr Thr Thr Ser Val Thr Leu Asp Arg Glu Glu His
            180                 185                 190

Ser Ser Tyr Thr Leu Thr Val Glu Ala Arg Asp Gly Asn Gly Glu Val
        195                 200                 205

Thr Asp Lys Pro Val Lys Gln Ala Gln Val Gln Ile Arg Ile Leu Asp
    210                 215                 220

Val Asn Asp Asn Ile Pro Val Val Glu Asn Lys Val Leu Glu Gly Met
225                 230                 235                 240

Val Glu Glu Asn Gln Val Asn Val Glu Val Thr Arg Ile Lys Val Phe
                245                 250                 255

Asp Ala Asp Glu Ile Gly Ser Asp Asn Trp Leu Ala Asn Phe Thr Phe
            260                 265                 270

Ala Ser Gly Asn Glu Gly Gly Tyr Phe His Ile Glu Thr Asp Ala Gln
        275                 280                 285

Thr Asn Glu Gly Ile Val Thr Leu Ile Lys Glu Val Asp Tyr Glu Glu
    290                 295                 300

Met Lys Asn Leu Asp Phe Ser Val Ile Val Ala Asn Lys Ala Ala Phe
305                 310                 315                 320

His Lys Ser Ile Arg Ser Lys Tyr Lys Pro Thr Pro Ile Pro Ile Lys
                325                 330                 335

Val Lys Val Lys Asn Val Lys Glu Gly Ile His Phe Lys Ser Ser Val
            340                 345                 350

Ile Ser Ile Tyr Val Ser Glu Ser Met Asp Arg Ser Ser Lys Gly Gln
        355                 360                 365

Ile Ile Gly Asn Phe Gln Ala Phe Asp Glu Asp Thr Gly Leu Pro Ala
    370                 375                 380

His Ala Arg Tyr Val Lys Leu Glu Asp Arg Asp Asn Trp Ile Ser Val

-continued

```
385                 390                 395                 400

Asp Ser Val Thr Ser Glu Ile Lys Leu Ala Lys Leu Pro Asp Phe Glu
                405                 410                 415

Ser Arg Tyr Val Gln Asn Gly Thr Tyr Thr Val Lys Ile Val Ala Ile
            420                 425                 430

Ser Glu Asp Tyr Pro Arg Lys Thr Ile Thr Gly Thr Val Leu Ile Asn
        435                 440                 445

Val Glu Asp Ile Asn Asp Asn Cys Pro Thr Leu Ile Glu Pro Val Gln
    450                 455                 460

Thr Ile Cys His Asp Ala Glu Tyr Val Asn Val Thr Ala Glu Asp Leu
465                 470                 475                 480

Asp Gly His Pro Asn Ser Gly Pro Phe Ser Phe Ser Val Ile Asp Lys
                485                 490                 495

Pro Pro Gly Met Ala Glu Lys Trp Lys Ile Ala Arg Gln Glu Ser Thr
            500                 505                 510

Ser Val Leu Leu Gln Gln Ser Glu Lys Lys Leu Gly Arg Ser Glu Ile
        515                 520                 525

Gln Phe Leu Ile Ser Asp Asn Gln Gly Phe Ser Cys Pro Glu Lys Gln
    530                 535                 540

Val Leu Thr Leu Thr Val Cys Glu Cys Leu His Gly Ser Gly Cys Arg
545                 550                 555                 560

Glu Ala Gln His Asp Ser Tyr Val Gly Leu Gly Pro Ala Ala Ile Ala
                565                 570                 575

Leu Met Ile Leu Ala Phe Leu Leu Leu Leu Leu Val Pro Leu Leu Leu
            580                 585                 590

Leu Met Cys His Cys Gly Lys Gly Ala Lys Gly Phe Thr Pro Ile Pro
        595                 600                 605

Gly Thr Ile Glu Met Leu His Pro Trp Asn Asn Glu Gly Ala Pro Pro
    610                 615                 620

Glu Asp Lys Val Val Pro Ser Phe Leu Pro Val Asp Gln Gly Gly Ser
625                 630                 635                 640

Leu Val Gly Arg Asn Gly Val Gly Gly Met Ala Lys Glu Ala Thr Met
                645                 650                 655

Lys Gly Ser Ser Ser Ala Ser Ile Val Lys Gly Gln His Glu Met Ser
            660                 665                 670

Glu Met Asp Gly Arg Trp Glu Glu His Arg Ser Leu Leu Ser Gly Arg
        675                 680                 685

Ala Thr Gln Phe Thr Gly Ala Thr Gly Ala Ile Met Thr Thr Glu Thr
    690                 695                 700

Thr Lys Thr Ala Arg Ala Thr Gly Ala Ser Arg Asp Met Ala Gly Ala
705                 710                 715                 720

Gln Ala Ala Ala Val Ala Leu Asn Glu Glu Phe Leu Arg Asn Tyr Phe
                725                 730                 735

Thr Asp Lys Ala Ala Ser Tyr Thr Glu Glu Asp Glu Asn His Thr Ala
            740                 745                 750

Lys Asp Cys Leu Leu Val Tyr Ser Gln Glu Glu Thr Glu Ser Leu Asn
        755                 760                 765

Ala Ser Ile Gly Cys Cys Ser Phe Ile Glu Gly Glu Leu Asp Asp Arg
    770                 775                 780

Phe Leu Asp Asp Leu Gly Leu Lys Phe Lys Thr Leu Ala Glu Val Cys
785                 790                 795                 800

Leu Gly Gln Lys Ile Asp Ile Asn Lys Glu Ile Glu Gln Arg Gln Lys
                805                 810                 815
```

-continued

Pro Ala Thr Glu Thr Ser Met Asn Thr Ala Ser His Ser Leu Cys Glu
820 825 830

Gln Thr Met Val Asn Ser Glu Asn Thr Tyr Ser Ser Gly Ser Ser Phe
835 840 845

Pro Val Pro Lys Ser Leu Gln Glu Ala Asn Ala Glu Lys Val Thr Gln
850 855 860

Glu Ile Val Thr Glu Arg Ser Val Ser Ser Arg Gln Ala Gln Lys Val
865 870 875 880

Ala Thr Pro Leu Pro Asp Pro Met Ala Ser Arg Asn Val Ile Ala Thr
885 890 895

Glu Thr Ser Tyr Val Thr Gly Ser Thr Met Pro Pro Thr Thr Val Ile
900 905 910

Leu Gly Pro Ser Gln Pro Gln Ser Leu Ile Val Thr Glu Arg Val Tyr
915 920 925

Ala Pro Ala Ser Thr Leu Val Asp Gln Pro Tyr Ala Asn Glu Gly Thr
930 935 940

Val Val Val Thr Glu Arg Val Ile Gln Pro His Gly Gly Gly Ser Asn
945 950 955 960

Pro Leu Glu Gly Thr Gln His Leu Gln Asp Val Pro Tyr Val Met Val
965 970 975

Arg Glu Arg Glu Ser Phe Leu Ala Pro Ser Ser Gly Val Gln Pro Thr
980 985 990

Leu Ala Met Pro Asn Ile Ala Val Gly Gln Asn Val Thr Val Thr Glu
995 1000 1005

Arg Val Leu Ala Pro Ala Ser Thr Leu Gln Ser Ser Tyr Gln Ile
1010 1015 1020

Pro Thr Glu Asn Ser Met Thr Ala Arg Asn Thr Thr Val Ser Gly
1025 1030 1035

Ala Gly Val Pro Gly Pro Leu Pro Asp Phe Gly Leu Glu Glu Ser
1040 1045 1050

Gly His Ser Asn Ser Thr Ile Thr Thr Ser Ser Thr Arg Val Thr
1055 1060 1065

Lys His Ser Thr Val Gln His Ser Tyr Ser
1070 1075

<210> SEQ ID NO 9
<211> LENGTH: 1098
<212> TYPE: PRT
<213> ORGANISM: Homo sapiens

<400> SEQUENCE: 9

Met Ala Arg Ser Pro Gly Arg Ala Tyr Ala Leu Leu Leu Leu Leu Ile
1 5 10 15

Cys Phe Asn Val Gly Ser Gly Leu His Leu Gln Val Leu Ser Thr Arg
20 25 30

Asn Glu Asn Lys Leu Leu Pro Lys His Pro His Leu Val Arg Gln Lys
35 40 45

Arg Ala Trp Ile Thr Ala Pro Val Ala Leu Arg Glu Gly Glu Asp Leu
50 55 60

Ser Lys Lys Asn Pro Ile Ala Lys Ile His Ser Asp Leu Ala Glu Glu
65 70 75 80

Arg Gly Leu Lys Ile Thr Tyr Lys Tyr Thr Gly Lys Gly Ile Thr Glu
85 90 95

Pro Pro Phe Gly Ile Phe Val Phe Asn Lys Asp Thr Gly Glu Leu Asn

-continued

```
            100                 105                 110

Val Thr Ser Ile Leu Asp Arg Glu Glu Thr Pro Phe Phe Leu Asn Asn
        115                 120                 125

Val Glu Lys Pro Leu Glu Leu Arg Ile Lys Val Leu Asp Ile Asn Asp
    130                 135                 140

Asn Glu Pro Val Phe Thr Gln Asp Val Phe Val Gly Ser Val Glu Glu
145                 150                 155                 160

Leu Ser Ala Ala His Thr Leu Val Met Lys Ile Asn Ala Thr Asp Ala
                165                 170                 175

Asp Glu Pro Asn Thr Leu Asn Ser Lys Ile Ser Tyr Arg Ile Val Ser
            180                 185                 190

Leu Glu Pro Ala Tyr Pro Pro Ile Tyr Thr Thr Ser Val Thr Leu Asp
        195                 200                 205

Arg Glu Glu His Ser Ser Tyr Thr Leu Thr Val Glu Ala Arg Asp Gly
    210                 215                 220

Asn Gly Glu Val Thr Asp Lys Pro Val Lys Gln Ala Gln Val Gln Ile
225                 230                 235                 240

Arg Ile Leu Asp Val Asn Asp Asn Ile Pro Val Val Glu Asn Lys Val
                245                 250                 255

Leu Glu Gly Met Val Glu Glu Asn Gln Val Asn Val Glu Val Thr Arg
            260                 265                 270

Ile Lys Val Phe Asp Ala Asp Glu Ile Gly Ser Asp Asn Trp Leu Ala
        275                 280                 285

Asn Phe Thr Phe Ala Ser Gly Asn Glu Gly Gly Tyr Phe His Ile Glu
    290                 295                 300

Thr Asp Ala Gln Thr Asn Glu Gly Ile Val Thr Leu Ile Lys Glu Val
305                 310                 315                 320

Asp Tyr Glu Glu Met Lys Asn Leu Asp Phe Ser Val Ile Val Ala Asn
                325                 330                 335

Lys Ala Ala Phe His Lys Ser Ile Arg Ser Lys Tyr Lys Pro Thr Pro
            340                 345                 350

Ile Pro Ile Lys Val Lys Val Lys Asn Val Lys Glu Gly Ile His Phe
        355                 360                 365

Lys Ser Ser Val Ile Ser Ile Tyr Val Ser Glu Ser Met Asp Arg Ser
    370                 375                 380

Ser Lys Gly Gln Ile Ile Gly Asn Phe Gln Ala Phe Asp Glu Asp Thr
385                 390                 395                 400

Gly Leu Pro Ala His Ala Arg Tyr Val Lys Leu Glu Asp Arg Asp Asn
                405                 410                 415

Trp Ile Ser Val Asp Ser Val Thr Ser Glu Ile Lys Leu Ala Lys Leu
            420                 425                 430

Pro Asp Phe Glu Ser Arg Tyr Val Gln Asn Gly Thr Tyr Thr Val Lys
        435                 440                 445

Ile Val Ala Ile Ser Glu Asp Tyr Pro Arg Lys Thr Ile Thr Gly Thr
    450                 455                 460

Val Leu Ile Asn Val Glu Asp Ile Asn Asp Asn Cys Pro Thr Leu Ile
465                 470                 475                 480

Glu Pro Val Gln Thr Ile Cys His Asp Ala Glu Tyr Val Asn Val Thr
                485                 490                 495

Ala Glu Asp Leu Asp Gly His Pro Asn Ser Gly Pro Phe Ser Phe Ser
            500                 505                 510

Val Ile Asp Lys Pro Pro Gly Met Ala Glu Lys Trp Lys Ile Ala Arg
        515                 520                 525
```

-continued

```
Gln Glu Ser Thr Ser Val Leu Leu Gln Gln Ser Glu Lys Lys Leu Gly
    530                 535                 540

Arg Ser Glu Ile Gln Phe Leu Ile Ser Asp Asn Gln Gly Phe Ser Cys
545                 550                 555                 560

Pro Glu Lys Gln Val Leu Thr Leu Thr Val Cys Glu Cys Leu His Gly
                565                 570                 575

Ser Gly Cys Arg Glu Ala Gln His Asp Ser Tyr Val Gly Leu Gly Pro
            580                 585                 590

Ala Ala Ile Ala Leu Met Ile Leu Ala Phe Leu Leu Leu Leu Leu Val
        595                 600                 605

Pro Leu Leu Leu Leu Met Cys His Cys Gly Lys Gly Ala Lys Gly Phe
    610                 615                 620

Thr Pro Ile Pro Gly Thr Ile Glu Met Leu His Pro Trp Asn Asn Glu
625                 630                 635                 640

Gly Ala Pro Pro Glu Asp Lys Val Val Pro Ser Phe Leu Pro Val Asp
                645                 650                 655

Gln Gly Gly Ser Leu Val Gly Arg Asn Gly Val Gly Gly Met Ala Lys
            660                 665                 670

Glu Ala Thr Met Lys Gly Ser Ser Ser Ala Ser Ile Val Lys Gly Gln
        675                 680                 685

His Glu Met Ser Glu Met Asp Gly Arg Trp Glu Glu His Arg Ser Leu
    690                 695                 700

Leu Ser Gly Arg Ala Thr Gln Phe Thr Gly Ala Thr Gly Ala Ile Met
705                 710                 715                 720

Thr Thr Glu Thr Thr Lys Thr Ala Arg Ala Thr Gly Ala Ser Arg Asp
                725                 730                 735

Met Ala Gly Ala Gln Ala Ala Ala Val Ala Leu Asn Glu Glu Phe Leu
            740                 745                 750

Arg Asn Tyr Phe Thr Asp Lys Ala Ala Ser Tyr Thr Glu Glu Asp Glu
        755                 760                 765

Asn His Thr Ala Lys Asp Cys Leu Leu Val Tyr Ser Gln Glu Glu Thr
    770                 775                 780

Glu Ser Leu Asn Ala Ser Ile Gly Cys Cys Ser Phe Ile Glu Gly Glu
785                 790                 795                 800

Leu Asp Asp Arg Phe Leu Asp Asp Leu Gly Leu Lys Phe Lys Thr Leu
                805                 810                 815

Ala Glu Val Cys Leu Gly Gln Lys Ile Asp Ile Asn Lys Glu Ile Glu
            820                 825                 830

Gln Arg Gln Lys Pro Ala Thr Glu Thr Ser Met Asn Thr Ala Ser His
        835                 840                 845

Ser Leu Cys Glu Gln Thr Met Val Asn Ser Glu Asn Thr Tyr Ser Ser
    850                 855                 860

Gly Ser Ser Phe Pro Val Pro Lys Ser Leu Gln Glu Ala Asn Ala Glu
865                 870                 875                 880

Lys Val Thr Gln Glu Ile Val Thr Glu Arg Ser Val Ser Ser Arg Gln
                885                 890                 895

Ala Gln Lys Val Ala Thr Pro Leu Pro Asp Pro Met Ala Ser Arg Asn
            900                 905                 910

Val Ile Ala Thr Glu Thr Ser Tyr Val Thr Gly Ser Thr Met Pro Pro
        915                 920                 925

Thr Thr Val Ile Leu Gly Pro Ser Gln Pro Gln Ser Leu Ile Val Thr
    930                 935                 940
```

```
Glu Arg Val Tyr Ala Pro Ala Ser Thr Leu Val Asp Gln Pro Tyr Ala
945                 950                 955                 960

Asn Glu Gly Thr Val Val Val Thr Glu Arg Val Ile Gln Pro His Gly
                965                 970                 975

Gly Gly Ser Asn Pro Leu Glu Gly Thr Gln His Leu Gln Asp Val Pro
            980                 985                 990

Tyr Val Met Val Arg Glu Arg Glu  Ser Phe Leu Ala Pro  Ser Ser Gly
        995                 1000                 1005

Val Gln  Pro Thr Leu Ala Met  Pro Asn Ile Ala Val  Gly Gln Asn
    1010                 1015                 1020

Val Thr  Val Thr Glu Arg Val  Leu Ala Pro Ala Ser  Thr Leu Gln
    1025                 1030                 1035

Ser Ser  Tyr Gln Ile Pro Thr  Glu Asn Ser Met Thr  Ala Arg Asn
    1040                 1045                 1050

Thr Thr  Val Ser Gly Ala Gly  Val Pro Gly Pro Leu  Pro Asp Phe
    1055                 1060                 1065

Gly Leu  Glu Glu Ser Gly His  Ser Asn Ser Thr Ile  Thr Thr Ser
    1070                 1075                 1080

Ser Thr  Arg Val Thr Lys His  Ser Thr Val Gln His  Ser Tyr Ser
    1085                 1090                 1095


<210> SEQ ID NO 10
<211> LENGTH: 10
<212> TYPE: PRT
<213> ORGANISM: Homo sapiens

<400> SEQUENCE: 10

Leu Thr Gly Tyr Ala Leu Asp Ala Arg Gly
1               5                   10


<210> SEQ ID NO 11
<211> LENGTH: 10
<212> TYPE: PRT
<213> ORGANISM: Homo sapiens

<400> SEQUENCE: 11

Tyr Thr Arg Leu Gly Ala Asn Leu Ala Gly
1               5                   10


<210> SEQ ID NO 12
<211> LENGTH: 15
<212> TYPE: PRT
<213> ORGANISM: Homo sapiens

<400> SEQUENCE: 12

Tyr Thr Thr Ser Val Thr Leu Asp Arg Glu Glu His Ser Ser Tyr
1               5                   10                  15


<210> SEQ ID NO 13
<211> LENGTH: 15
<212> TYPE: PRT
<213> ORGANISM: Homo sapiens

<400> SEQUENCE: 13

Ala Arg Asp Gly Asn Gly Glu Val Thr Asp Lys Pro Val Lys Gln
1               5                   10                  15


<210> SEQ ID NO 14
<211> LENGTH: 10
<212> TYPE: PRT
<213> ORGANISM: Homo sapiens
```

```
<400> SEQUENCE: 14

Ile Val Ser Leu Glu Pro Ala Tyr Pro Pro
1               5                   10
```